United States Patent
Raby et al.

(10) Patent No.: US 8,517,727 B2
(45) Date of Patent: Aug. 27, 2013

(54) AUTOMATIC ADJUSTMENT OF AN ORTHODONTIC BRACKET TO A DESIRED OCCLUSAL HEIGHT WITHIN A THREE-DIMENSIONAL (3D) ENVIRONMENT

(75) Inventors: Richard E. Raby, North St. Paul, MN (US); Nicholas A. Stark, Cottage Grove, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 2236 days.

(21) Appl. No.: 10/903,686

(22) Filed: Jul. 30, 2004

(65) Prior Publication Data

US 2006/0024637 A1 Feb. 2, 2006

(51) Int. Cl.
*A61C 3/00* (2006.01)

(52) U.S. Cl.
USPC .......................................................... 433/24

(58) Field of Classification Search
USPC .......................................................... 433/24
See application file for complete search history.

(56) References Cited

U.S. PATENT DOCUMENTS

| | | | |
|---|---|---|---|
| 5,879,158 A | 3/1999 | Doyle et al. | |
| 6,099,314 A | 8/2000 | Kopelman et al. | |
| 6,123,544 A | 9/2000 | Cleary | |
| 6,152,731 A | 11/2000 | Jordan et al. | |
| 6,318,994 B1 | 11/2001 | Chishti et al. | |
| 6,322,359 B1 | 11/2001 | Jordan et al. | |
| 6,334,772 B1 | 1/2002 | Taub et al. | |
| 6,334,853 B1 | 1/2002 | Kopelman et al. | |
| 6,457,978 B1 | 10/2002 | Cloonan et al. | |
| 6,632,089 B2 | 10/2003 | Rubbert et al. | |
| 6,664,986 B1 | 12/2003 | Kopelman et al. | |
| 6,695,613 B2 | 2/2004 | Taub et al. | |
| 6,697,164 B1 | 2/2004 | Babayoff et al. | |
| 6,739,869 B1 | 5/2004 | Taub et al. | |
| 7,029,275 B2 | 4/2006 | Rubbert et al. | |
| 7,033,327 B2 | 4/2006 | Raby | |
| 7,080,979 B2 | 7/2006 | Rubbert et al. | |
| 2002/0150859 A1 | 10/2002 | Imgrund et al. | |
| 2002/0156652 A1 | 10/2002 | Sachdeva et al. | |
| 2003/0003416 A1 | 1/2003 | Chishti et al. | |

(Continued)

FOREIGN PATENT DOCUMENTS

DE 42 34 661 4/1993
JP 5-261124 10/1993

(Continued)

OTHER PUBLICATIONS

U.S. Appl. No. 10/734,323, "Method of Placing Orthodontic Brackets on Teeth in a 3D Virtual World," filed Dec. 12, 2003.

(Continued)

*Primary Examiner* — Heidi M Eide

(57) ABSTRACT

A system automatically adjusts an orthodontic bracket to a desired occlusal height on a tooth within a 3D environment. The system allows a practitioner to specify a desired occlusal height at which to place the bracket on the tooth. The practitioner may choose the desired occlusal height from a standardized set of occlusal heights or may create a customized occlusal height to meet a patient's particular needs. Based on the desired occlusal height, the system automatically adjusts the placement of the orthodontic bracket to the desired occlusal height on the tooth within the 3D environment. The system then generates a visual representation the resulting bracket placement within the 3D environment.

54 Claims, 37 Drawing Sheets

(56) References Cited

U.S. PATENT DOCUMENTS

| | | | |
|---|---|---|---|
| 2003/0021453 A1* | 1/2003 | Weise et al. | 382/128 |
| 2003/0163291 A1 | 8/2003 | Jordan et al. | |
| 2003/0215764 A1 | 11/2003 | Kopelman et al. | |
| 2003/0219692 A1 | 11/2003 | Kopelman et al. | |
| 2003/0224316 A1 | 12/2003 | Marshall | |
| 2004/0029078 A1 | 2/2004 | Marshall | |
| 2004/0054304 A1 | 3/2004 | Raby | |
| 2004/0115586 A1 | 6/2004 | Andreiko et al. | |
| 2004/0142297 A1 | 7/2004 | Taub et al. | |
| 2004/0142298 A1 | 7/2004 | Taub et al. | |
| 2004/0214128 A1* | 10/2004 | Sachdeva et al. | 433/24 |
| 2005/0191593 A1 | 9/2005 | Knopp | |

FOREIGN PATENT DOCUMENTS

| | | |
|---|---|---|
| JP | 2004-504077 | 2/2004 |
| WO | 97/03622 | 2/1997 |
| WO | WO 03/073382 A1 | 9/2003 |

OTHER PUBLICATIONS

U.S. Appl. No. 10/771,641, "Planar Guides to Visually Aid Orthodontic Appliance Placement with a Three-Dimensional (3D) Environment," filed Feb. 4, 2004.

U.S. Appl. No. 10/959,624, "Placing Orthodontic Objects Along an Archwire Within a Three-Dimensional (3D) Environment", filed Oct. 6, 2004.

U.S. Appl. No. 10/959,625, "Movement of Orthodontic Objects Along a Virtual Archwire within a Three-Dimensional (3D) Environment", filed Oct. 6, 2004.

\* cited by examiner

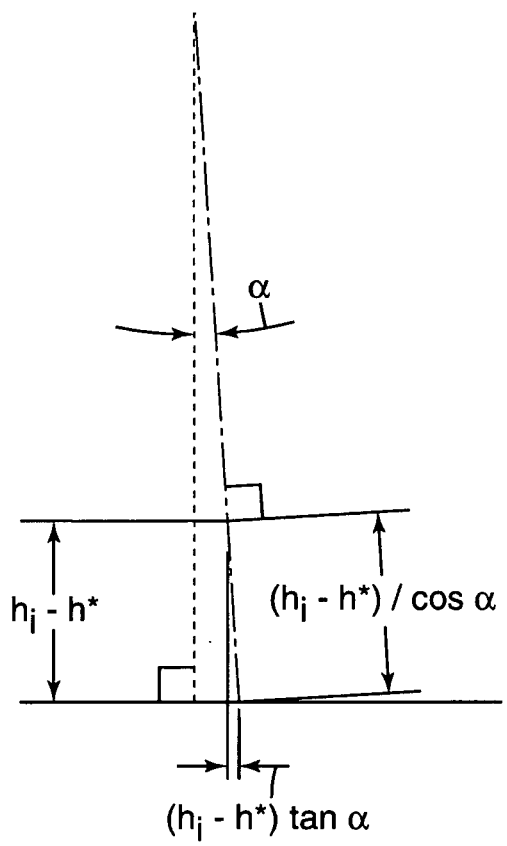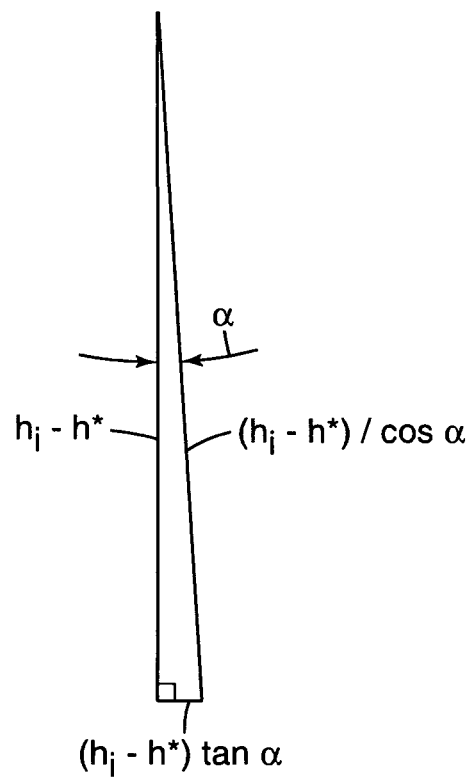
*Fig. 4C*  *Fig. 4D*

AUTOMATIC ADJUSTMENT OF AN ORTHODONTIC BRACKET TO A DESIRED OCCLUSAL HEIGHT WITHIN A THREE-DIMENSIONAL (3D) ENVIRONMENT

TECHNICAL FIELD

The invention relates to electronic orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, which are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly or torqued from one appliance to the next in accordance with the patient's malocclusions. However, the resiliency of the archwire tends to return the archwire to its normally curved shape that lies in the flat reference plane. As the archwire shifts toward the flat reference plane, the attached teeth are moved in a corresponding fashion toward an aligned, aesthetically pleasing array.

As can be appreciated, it is important for the practitioner using straight wire appliances to precisely fix each bracket in the proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal directions, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the invention relates to techniques for assisting practitioners in orthodontic diagnosis and treatment. More specifically, a system is described that provides an environment for modeling and depicting a three-dimensional (3D) representation of a patient's dental arch. By interacting with the system, orthodontic practitioners are able to visualize the 3D representation of the dental arch, and precisely position "virtual" orthodontic appliances relative to the modeled dental arch. For example, the orthodontic practitioner may interact with the system to position brackets on one or more teeth within the modeled dental arch.

As described in detail herein, the system allows the practitioner to define a desired occlusal height at which a bracket is to be placed on a tooth. The occlusal height may be defined as the distance from a bracket origin (e.g., the center of the base of the bracket slot) to an occlusal-most point on the tooth measured along the occluso-gingival axis of the tooth. In another embodiment, the occlusal height may be defined as the distance from the bracket origin to an occlusal-most plane for the entire dental arch measured along the occluso-gingival axis of the tooth. The desired occlusal height may be chosen from a standardized set of occlusal heights or may be customized by the practitioner to the particular needs of a patient.

Based on the defined occlusal height, the system automatically adjusts position and orientation of a virtual bracket within the 3D environment. The system may include two methods of automatically adjusting an orthodontic bracket to a desired occlusal height on the tooth. One embodiment allows the practitioner to specify the desired occlusal height. The system then automatically, through a series of iterations, adjusts the actual occlusal height of the bracket until the actual occlusal height closely approximates the desired occlusal height. Another embodiment also allows the practitioner to specify the desired occlusal height. This embodiment sections the tooth into a labial and a lingual portion and refers to one of the portions of the tooth during the automatic adjustment process.

Once the updated location and orientation have been computed, the system visually represents the resulting bracket placement within the 3D environment. The automatic bracket adjustment and the visual representation aid the practitioner in achieving the desired bracket placement on the tooth.

In one embodiment, the invention is directed to a method comprising rendering a digital representation of at least a portion of a tooth within a three-dimensional (3D) environment, receiving a desired occlusal height for an orthodontic appliance associated with the tooth, and automatically adjusting the orthodontic appliance to the desired occlusal height on the tooth within the 3D environment.

In another embodiment, the invention is directed to a system comprising a computing device, and modeling software executing on the computing device, wherein the modeling software comprises a rendering engine that renders a digital representation of at least a portion of a tooth within a three-dimensional (3D) environment, and an occlusal height control module that automatically adjusts an orthodontic appliance to a desired occlusal height on the tooth within the 3D environment.

In another embodiment, the invention is directed to a computer-readable medium containing instructions. The instructions cause a programmable processor to render a digital representation of at least a portion of a tooth within a three-dimensional (3D) environment, receive a desired occlusal height for an orthodontic appliance associated with the tooth; and automatically adjust the orthodontic appliance to the desired occlusal height on the tooth.

The details of one or more embodiments of the invention are set forth in the accompanying drawings and the descrip-

BRIEF DESCRIPTION OF DRAWINGS

FIGS. 4A-4D are diagrams illustrating an anterior tooth with an orthodontic bracket and bracket base coordinate systems used to determine bracket translation distance.

DETAILED DESCRIPTION

Figure 1:
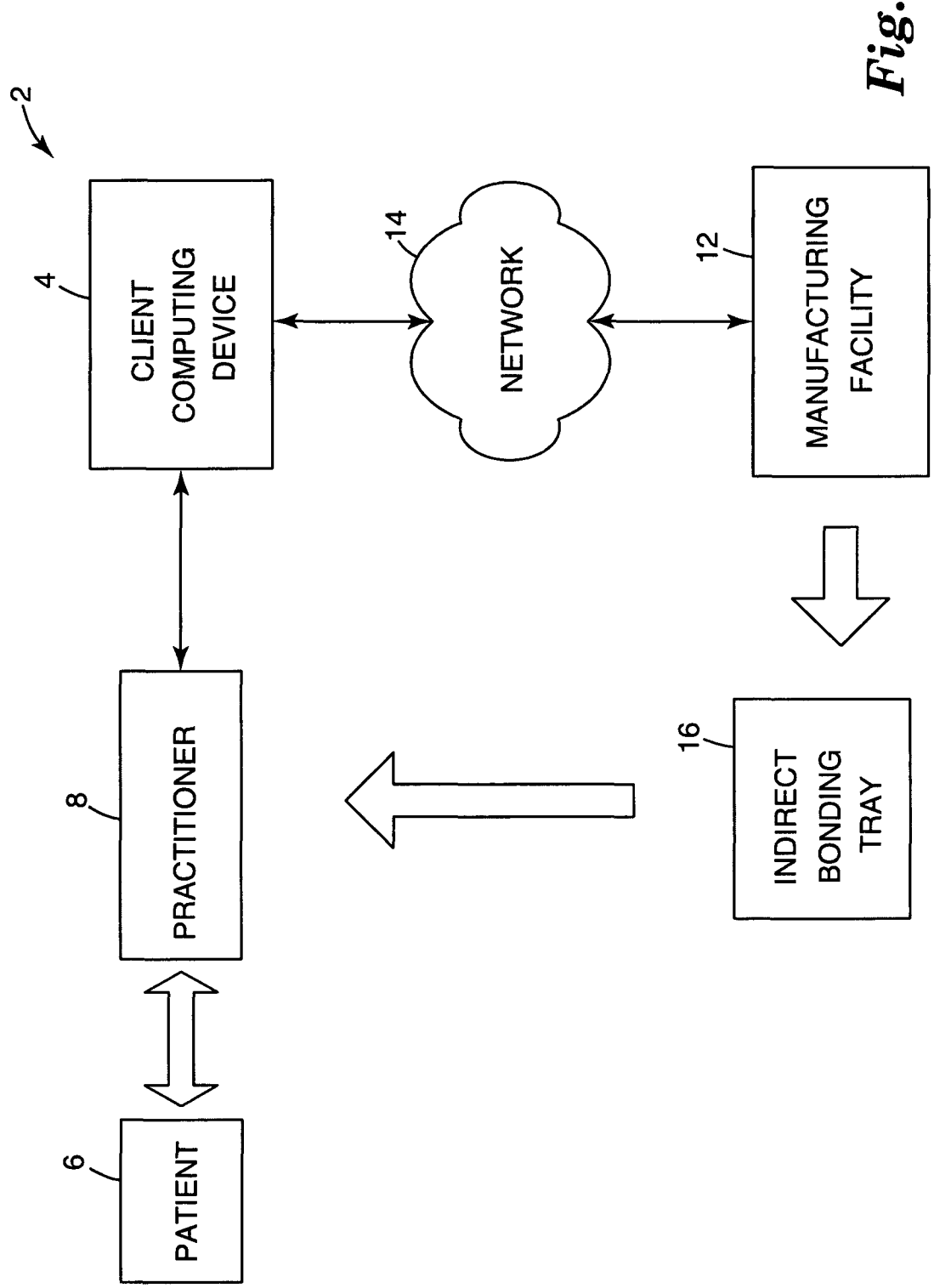
FIG. 1 is a block diagram illustrating an exemplary computer environment in which a client computing device automatically adjusts an orthodontic appliance (e.g., bracket) on a tooth in a three-dimensional (3D) environment.

FIG. 1 is a block diagram illustrating an exemplary computer environment 2 in which a client computing device 4 presents an environment for modeling a three-dimensional (3D) representation of a dental arch of patient 6. Orthodontic practitioner 8 interacts with modeling software executing on client computer device 4 to visualize the 3D representation of the dental arch, and precisely position "virtual" appliances (brackets, for example) on individual teeth within the modeled dental arch.

The 3D representation of the dental arch may be initially generated by digitally scanning a physical dental impression of the teeth of patient 6 or by scanning a casting made from the impression. Alternatively, practitioner 8 may use an intraoral scanner to produce the 3D digital representation directly from the teeth of patient 6. Other methods of scanning could also be used. Practitioner 8 may interact with the modeling software to view the 3D digital representation of the teeth and select the point on each tooth where the respective bracket is to be located. During this process, the modeling software manipulates each bracket as a separate object within the 3D environment, and fixes the position of each bracket within the 3D space relative to a coordinate system associated with the bracket's respective tooth. Consequently, practitioner 8 is able to independently view and precisely locate each bracket within the 3D environment relative to its respective tooth.

Although the description will generally discuss the display and positioning of orthodontic brackets, it shall be understood that client computing device 4 may display and/or position any type of orthodontic appliance without departing from the scope of the present invention. Examples of such orthodontic appliances include orthodontic brackets, buccal tubes, sheaths, buttons or archwires. In addition, client computing device 4 need not display a full visual representation of the appliance. Rather, a portion of the appliance may be displayed. As another alternative, client computing device 4 need not display the appliance itself. Rather, another object associated with an appliance or with the placement of an appliance may be shown instead of or in addition to the appliance itself. Examples of such other objects include crosshairs (intersecting lines indicating the position on a tooth where the center of an appliance is to be placed), placement jigs, placement guides, or other peripheral which may represent or be attached to an appliance, or which may be otherwise associated with an appliance and/or its placement. The terms "appliance" or "bracket" as used herein shall therefore be understood to include any type of appliance, a full or partial representation of an appliance, or any object associated with an appliance and/or its placement.

Client computing device 4 may show a digital representation of an entire dental arch, a portion of a dental arch, an individual tooth within the dental arch, or a portion of a tooth within the dental arch, or some combination thereof for viewing by the practitioner. Client computing device 4 may also show a digital representation of appliances on all of the teeth in a dental arch, the appliances on a portion of the teeth in a dental arch, an appliance on a single tooth, or an appliance on a portion of a tooth. Similarly, client computing device 4 may show a digital representation of an entire appliance, a portion of an appliance, or simply the crosshairs of an appliance (which may indicate, for example, the location on a tooth where the center of the appliance is to be placed). It shall be understood, therefore, that the image presented to the practitioner 8 by client computing device 4 may take many different forms, and that the invention is not limited in this respect.

As described in detail herein, the modeling software automatically adjusts an orthodontic bracket to a desired occlusal height on a tooth within the 3D environment. The brackets may initially be placed in the 3D environment using the method described in copending and commonly assigned U.S. patent application Ser. No. 10/734,323, entitled "Method of Placing Orthodontic Brackets on Teeth in a 3D Virtual World", filed Dec. 12, 2003 to Raby, et al., which is incorporated herein by reference in its entirety. Manual adjustment of orthodontic brackets may be assisted by use of visual planar guides, as described in copending and commonly assigned U.S. patent application Ser. No. 10/771,641, entitled "Planar Guides to Visually Aid Orthodontic Appliance Placement within a Three-Dimensional (3D) Environment", filed Feb. 4, 2004 to Raby, et al., which is incorporated herein by reference in its entirety. In that application, a system visually aids the user in manual placement of brackets through manual adjustments to bracket position and orientation.

In accordance with the techniques described herein, the modeling software automatically adjusts an orthodontic bracket within the 3D environment to a desired occlusal height on a tooth while simultaneously maintaining a desired fit between the bracket base and the tooth. In some embodiments, the practitioner specifies a desired occlusal height at which the bracket is to be placed. Based on this desired occlusal height, the modeling software automatically adjusts the placement of the orthodontic bracket to the desired occlusal height on the tooth within the 3D environment.

Once the brackets are placed and the practitioner has indicated his or her approval, client computing device 4 communicates the bracket placement positions to manufacturing facility 12 via network 14. In response, manufacturing facility constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Figure 2:
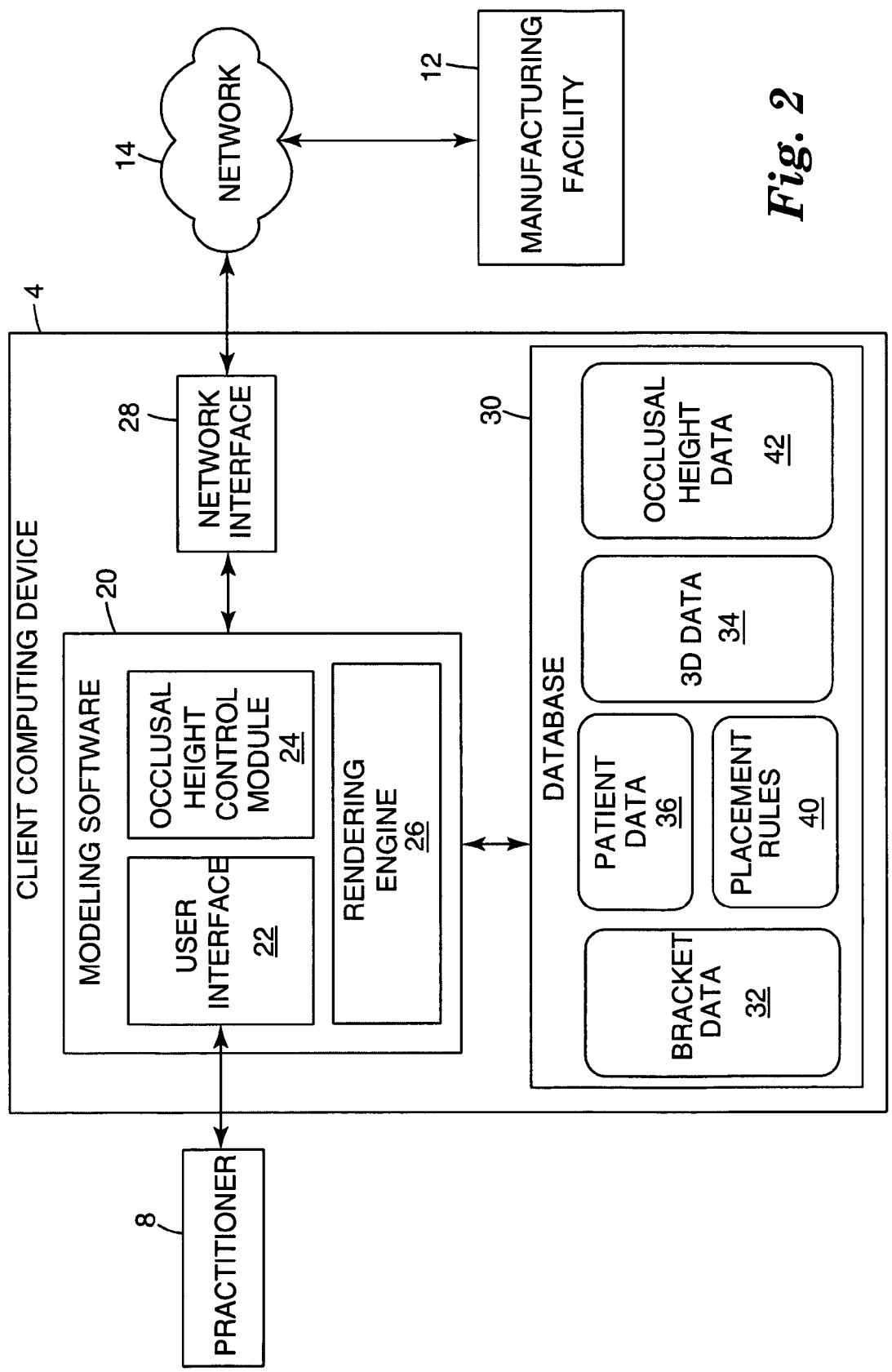
FIG. 2 is a block diagram illustrating an example embodiment of the client computing device of FIG. 1 in further detail.

FIG. 2 is a block diagram illustrating an example embodiment of client computing device 4 in further detail. In the illustrated embodiment, client computing device 4 provides an operating environment for modeling software 20. As described above, modeling software 20 presents a modeling environment for modeling and depicting the 3D representation of the teeth of patient 6 (FIG. 1). In the illustrated embodiment, modeling software 20 includes a user interface 22, an occlusal height control module 24, and a rendering engine 26.

User interface 22 provides a graphical user interface (GUI) that visually displays the 3D representation of the patient's teeth as well as 3D representations of the brackets. In addition, user interface 22 provides an interface for receiving input from practitioner 8, e.g., via a keyboard and a pointing device, for manipulating the brackets and placing the brackets on respective teeth within the modeled dental arch.

Modeling software 20 interacts with database 30 to access a variety of data, such as bracket data 32, 3D data 34, patient data 36, placement rules 40 and occlusal height data 42. Database 30 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS) or object relational (ORDBMS) database management system. The data may, for example, be stored within a single relational database such as SQL Server from Microsoft Corporation. Although illustrated as local to client computer device 4, database 30 may be located remote from the client computing device and coupled to the client computing device via a public or private network, e.g., network 14.

Bracket data 32 describes a set of commercially available brackets that may be selected by practitioner 8 and positioned within the 3D modeling environment. For example, bracket data 32 may store a variety of attributes for the commercially available brackets, such as dimensions, slot locations and characteristics, torque angles, angulations and other attributes. User interface 22 provides a menu-driven interface by which practitioner 8 selects the type of brackets for use in defining an orthodontic prescription for patient 6.

Patient data 36 describes a set of one or more patients, e.g., patient 6, associated with practitioner 8. For example, patient data 36 specifies general information, such as a name, birth date, and a dental history, for each patient. In addition, patient data 36 specifies a current prescription specified for each of the patients, including the types of brackets selected by practitioner 8 for use with each of the patients.

Occlusal height data 42 specifies a set of occlusal heights and may be input, for example, via user interface 22 by practitioner 8 for each tooth in the dentition. Occlusal height is one aspect of a patient's orthodontic prescription and, in one embodiment, is defined as the distance from the bracket origin (the center of the base of the bracket slot) to the occlusal-most point on the tooth, measured in the bracket slot coordinate system along the occlusal-gingival axis. Other definitions may readily be used. For example, the bracket origin may be defined as the occlusal-most point of the bracket slot, the occlusal-most point of the bracket, the gingival-most point of the bracket or any other point of reference relative to the bracket. The prescribed occlusal height affects functional occlusion at the conclusion of orthodontic treatment and the resulting aesthetic appearance of the teeth.

The orthodontic industry has developed standard prescriptions for many commercially available orthodontic brackets. These standardized prescriptions generally include, among other aspects of a prescription, a set of occlusal heights that tend to satisfy the functional and the aesthetic requirements of most patients. The standardized prescriptions may be used to achieve uniformity among patients or to avoid the more time consuming process of devising a custom set of occlusal heights for each individual patient. User interface 22 allows practitioner 8 to select one or more occlusal heights from the standardized prescriptions.

With some patients, practitioner 8 may desire to create a customized set of occlusal heights to achieve a more aesthetically pleasing result, or to better take into account that patient's malocclusion. User interface 22 allows a practitioner to quantify the desired occlusal heights for each tooth as part of an overall prescription for a patient, whether the prescribed heights are customized or standardized. For some patients, a standardized set of occlusal heights for the teeth in the dentition may be satisfactory. Alternatively, practitioner 8 may create a customized set of occlusal heights for the teeth in the dentition. As another example, a combination of standardized and customized occlusal heights throughout the dentition may be used. Practitioner 8 inputs the desired occlusal heights via user interface 22, which are then stored in database 30 as occlusal height data 42. Modeling software 20 then adjusts the brackets to the prescribed occlusal heights automatically, and stores the result in patient data 36.

Occlusal height control module 24 receives the occlusal height data 42 and automatically adjusts the occlusal height of the brackets associated with each tooth in accordance with the desired occlusal height. In addition, occlusal height control module 24 maintains a fit between the bracket base and the surface of the tooth.

Placement rules 40 may specify industry-defined placement rules for commercially available brackets. In addition, placement rules 40 may include user-defined rules specified by practitioner 8 or other rules for controlling bracket placement. For example, one rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a base of the bracket on the FACC of the tooth equidistant from the occlusal edge or occlusal-most point on the FACC and the gingival margin of the crown. This location is also known as the Facial Axis Point (FA Point). By automatically adjusting the bracket to a specified occlusal height, modeling software 20 may allow the practitioner 8 to place the orthodontic appliance on the tooth so that certain placement rules are satisfied.

As another example, practitioner 8 may desire to place brackets at an occlusal height that is different from the FA Point. Consequently, practitioner 8 may specify different occlusal heights for different types of teeth in the dentition, for different types of brackets, or both. Optionally, the desired occlusal heights may be based in whole or in part on known rules associated with a particular type, or prescription, of the appliances selected by practitioner 8.

Figure 3A:
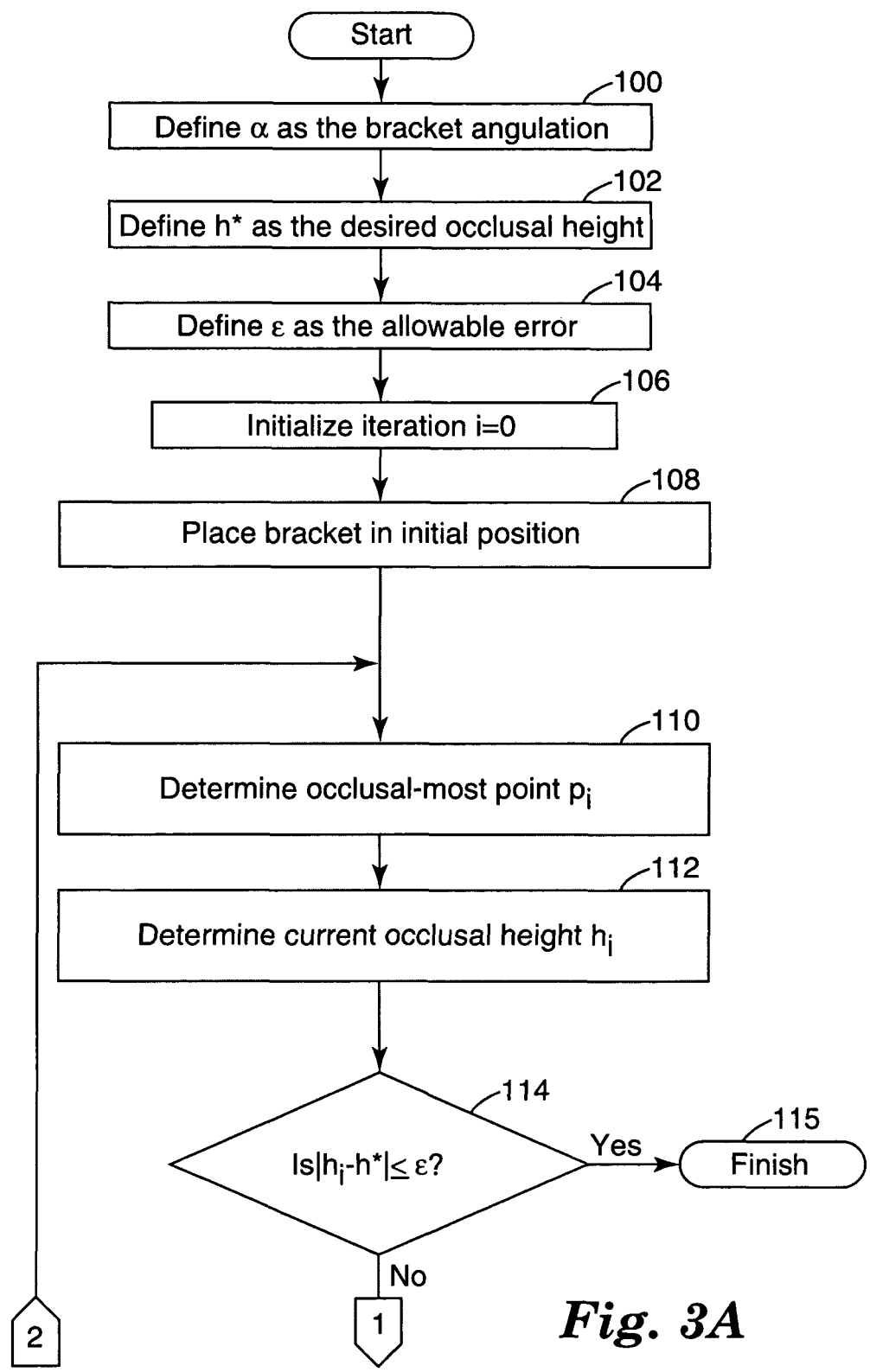
FIGS. 3A and 3B are a flowchart illustrating an example embodiment of a method of automatic orthodontic bracket adjustment.
Figure 3B:
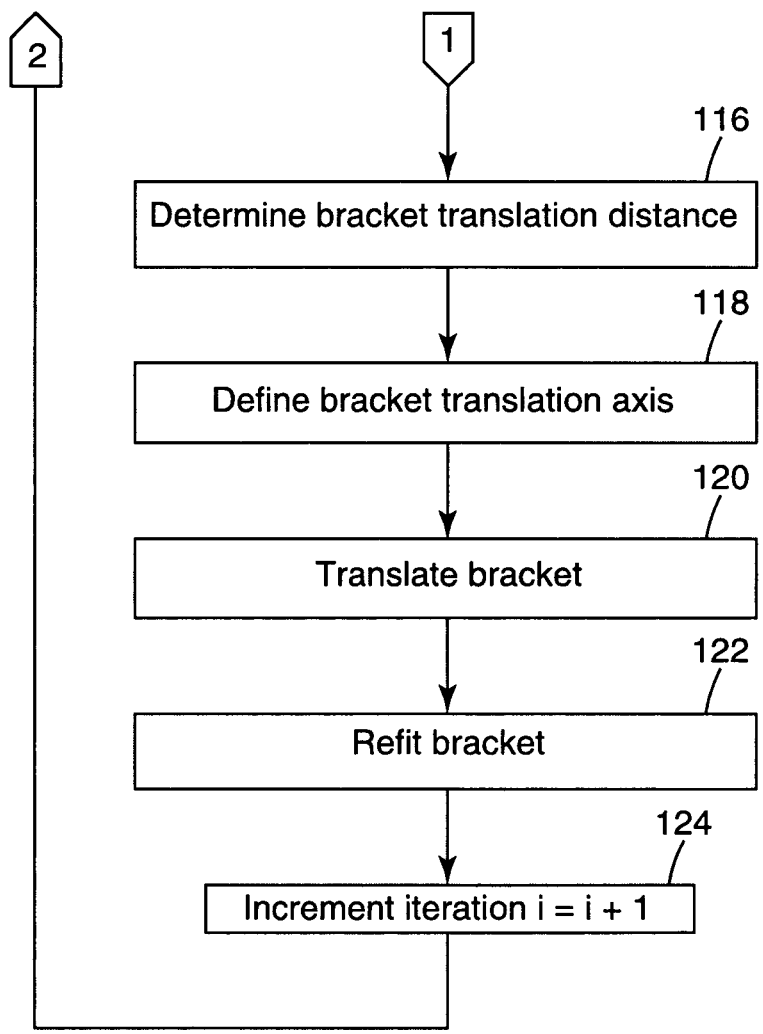

Rendering engine 26 accesses and renders 3D data 34 to generate the 3D view presented to practitioner 8 by user interface 22. More specifically, 3D data 34 includes information defining the 3D objects that represent each tooth and bracket within the 3D environment. Rendering engine 26 processes each object to render a 3D triangular mesh based on viewing perspective of practitioner 8 within the 3D environment. User interface 22 displays the rendered 3D triangular mesh to practitioner 8, and allows the practitioner to change viewing perspectives and manipulate objects within the 3D environment FIGS. 3A and 3B are a flowchart illustrating one example method of automatically adjusting an orthodontic bracket to a desired occlusal height on a tooth. More specifically, the flowchart of FIGS. 3A and 3B illustrates operation of modeling software 20 in automatically adjusting orthodontic brackets within the 3D virtual environment. The method shown in FIGS. 3A and 3B may be used on anterior teeth (incisor or cuspid) as well as on posterior teeth (bicuspid or molar). The method shown in FIGS. 3A and 3B will be described with respect to an anterior tooth (incisor or cuspid), such as that shown in FIGS. 4A and 4B.

Figure 4A:
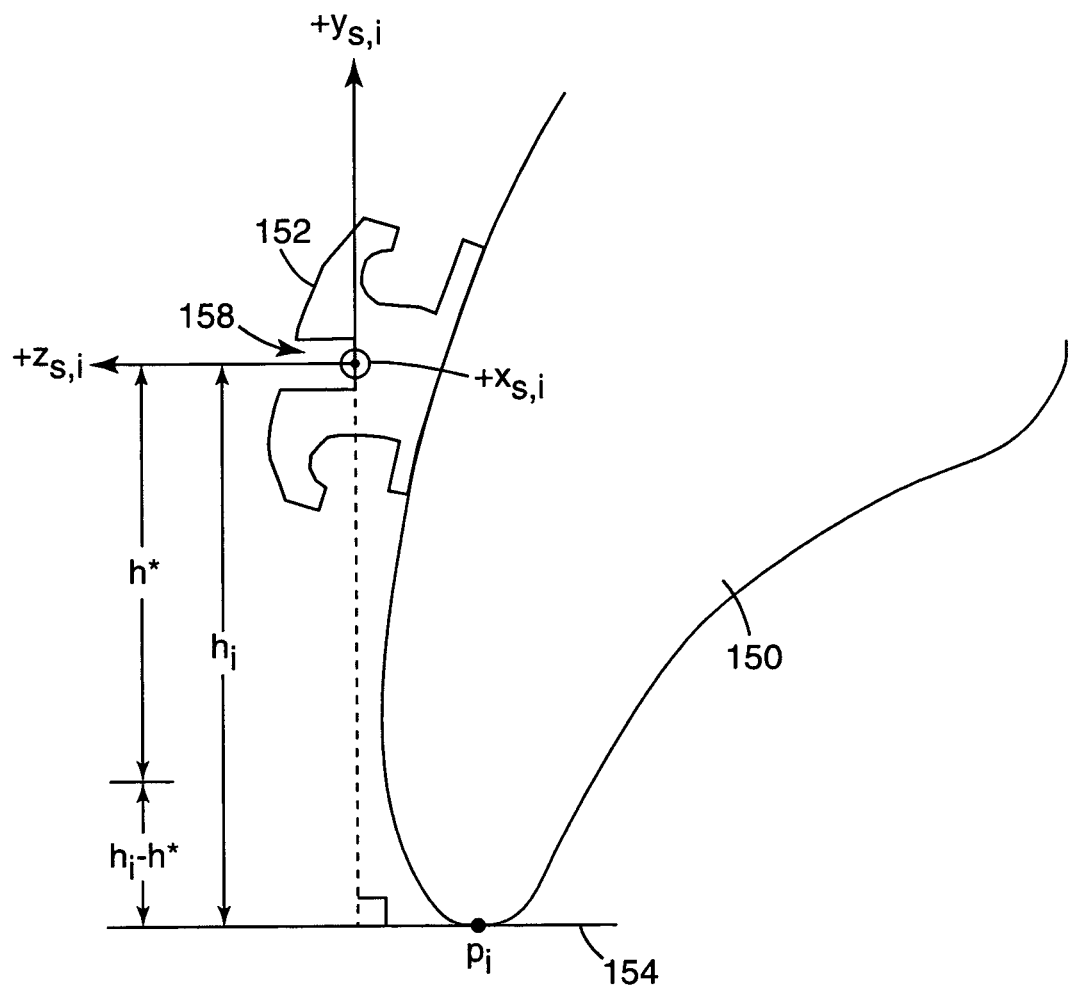
Figure 4B:
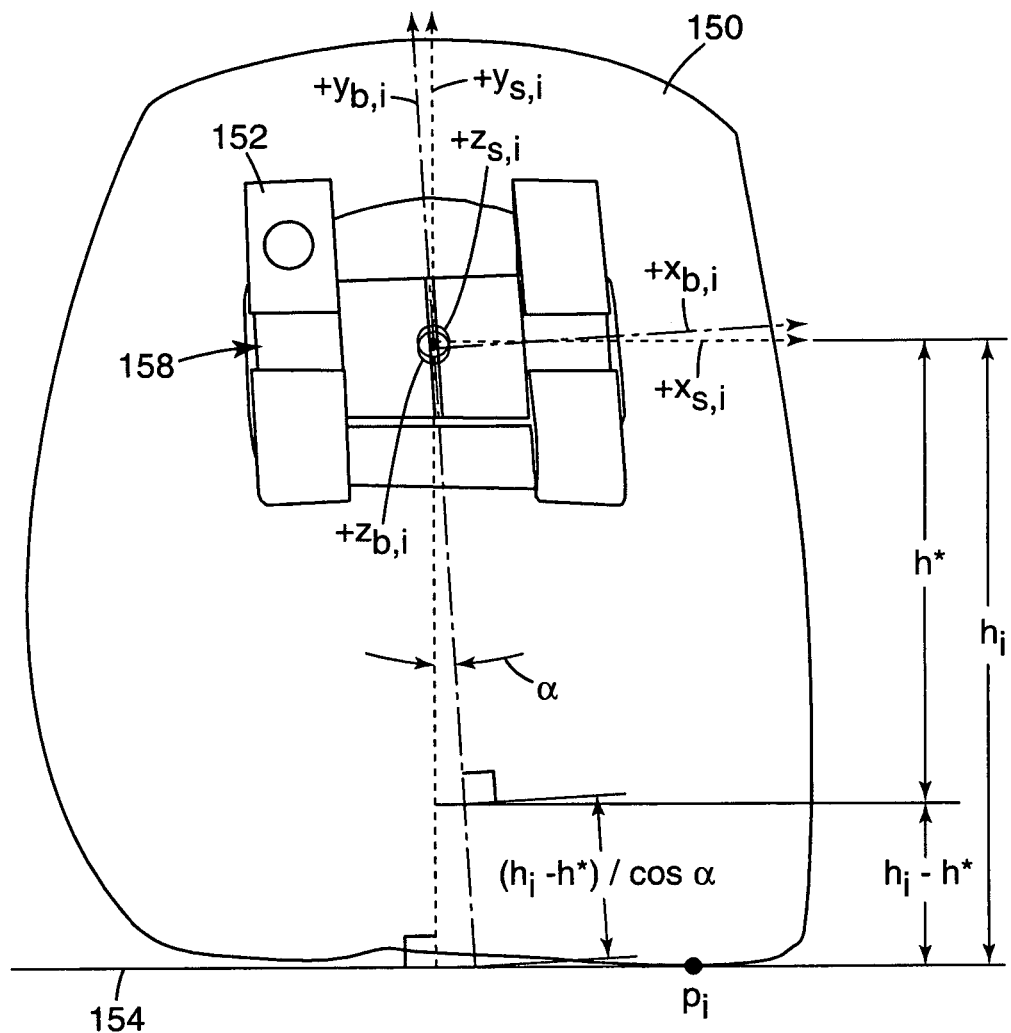

In general, FIG. 4A shows a mid-sagittal cross-section of an anterior tooth 150 with an orthodontic bracket 152 whose base is in contact with the tooth 150. FIG. 4B shows a facial view of the anterior tooth 150 of FIG. 4A. The $x_{s,i}$, $y_{s,i}$, $z_{s,i}$ axes form the bracket slot coordinate system of bracket 152. In this notation, "s" indicates the slot coordinate system and "i" indicates the iteration number through the automatic bracket adjustment process. In one embodiment, the $x_{s,i}$ axis of the slot coordinate system is parallel to the slot 158 of bracket 152. Also, both the slot 158 and the $x_{s,i}$ axis are parallel to the occlusal plane 154 of tooth 150. The $y_{s,i}$ axis is perpendicular to the $x_{s,i}$ axis (and therefore perpendicular to the slot 158 of bracket 152).

The $x_{b,i}$, $y_{b,i}$, $z_{b,i}$ axes form the base coordinate system. In this notation, "b" indicates the base coordinate system and "i" indicates the iteration number through the automatic adjustment process. In one embodiment, the $y_{b,i}$ axis of the base coordinate system is aligned parallel to the longitudinal axis of the tooth, or in other words, the $y_{b,i}$ axis is aligned parallel to mid-sagittal plane of the tooth. The $y_{b,i}$ axis is therefore not necessarily perpendicular to the slot 158 of bracket 152. Similarly, the horizontal ($x_{b,i}$) axis is therefore not necessarily parallel to slot 158.

For purposes of this example, "occlusal height" ($h_i$) is defined as the distance from the bracket origin (the center of the bottom of the bracket slot) to the occlusal-most point ($p_i$) on the tooth, measured in the bracket slot coordinate system along the occluso-gingival ($y_{s,i}$) axis. The desired occlusal height (h*) is defined as the desired occlusal height specified by the practitioner, whether that occlusal height is part of a customized set of occlusal heights unique to a particular patient or a part of a standardized set of occlusal heights.

The bracket angulation α is defined as the angle between the $y_{s,i}$ axis of the bracket slot coordinate system and the $y_{b,i}$ axis of the base coordinate system. In other words, the bracket angulation α is the difference between the longitudinal axis of the tooth and an axis that is perpendicular to the slot 158 (the axis perpendicular to the occlusal plane of the tooth in this embodiment).

Referring again to the method of FIGS. 3A and 3B, occlusal height control module 24 defines a as the bracket angulation (100) at the beginning of the automatic adjustment process. The bracket angulation is dependent in part on the type of bracket, the tooth geometry, and the initial placement of the bracket on the tooth. In addition, occlusal height control module 24 defines the quantity h* (102) as the desired occlusal height specified by the practitioner. Occlusal height control module 24 further defines the quantity ϵ (104) as the allowable error between the current occlusal height ($h_i$) and the desired occlusal height (h*). The allowable error may be indicated as an absolute distance (such as 0.01 millimeters), as a percentage of the occlusal height (such as less than 1% of the actual or desired occlusal height) or in any other appropriate manner. The iteration number (i) is initialized to zero (106) the first time through the automatic adjustment process.

Modeling software 20 places a bracket in an initial position on the facial surface of one of the teeth within the modeled dental arch (108). In one embodiment, the bracket is positioned such that axis $y_{b,0}$ of bracket base coordinate system ($x_{b,0}$, $y_{b,0}$, $z_{b,0}$) aligns with the FACC of tooth 150 (108). Modeling software 20 may accomplish this using the method described in the above-referenced copending and commonly assigned U.S. patent application Ser. No. 10/734,323. Generally, U.S. patent application Ser. No. 10/734,323 describes a method of placing a bracket on a tooth to attain a close, mating fit between the base of the bracket and the tooth surface.

Next, occlusal height control module 24 determines, for iteration i, the occlusal-most point $p_i$ on the tooth relative to the bracket slot coordinate system $x_{s,i}$, $y_{s,i}$, $z_{s,i}$ (110). FIGS. 4A and 4B illustrate this point in the automatic adjustment process. FIG. 4A shows a mid-sagittal cross-section of an anterior tooth with an orthodontic bracket whose base is in contact with the tooth. Shown are the bracket slot coordinate system ($x_{s,i}$, $y_{s,i}$, $z_{s,i}$), occlusal-most point $p_i$ relative to this coordinate system, current occlusal height $h_i$, desired occlusal height h*, and occlusal height difference $h_i$–h*.

FIG. 4B shows a facial view of the anterior tooth shown in FIG. 4A. Shown are the bracket base coordinate system ($x_{b,i}$, $y_{b,i}$, $z_{b,i}$), bracket slot coordinate system ($x_{s,i}$, $y_{s,i}$, $z_{s,i}$), occlusal-most point $p_i$ relative to this coordinate system, current occlusal height $h_i$, desired occlusal height h*, $h_i$–h*, bracket angulation α, and bracket translation distance ($h_i$–h*)/cosine (α).

Referring again to FIG. 3A, occlusal height control module 24 determines the current occlusal height $h_i$ (112). In one embodiment, occlusal height control module 24 determines the current occlusal height based on the occlusal most point $p_i$ in the bracket slot coordinate system $x_{s,i}$, $y_{s,i}$, $z_{s,i}$. If the absolute value of $h_i$–h* is less than the allowable error ϵ (114), then the bracket need not be adjusted further and the automatic bracket adjustment process for that bracket is finished (115).

If the absolute value of $h_i$–h* is greater than ϵ (114), then the process continues as shown in FIG. 3B. Occlusal height control module 24 determines the bracket translation distance, i.e., the amount that the bracket should be moved along the $y_{s,i}$ axis, based on the current occlusal height $h_i$, the desired occlusal height h*, and the bracket angulation α (116). As discussed above, in one embodiment, the bracket angulation a remains constant during the bracket translation process. The quantities $h_i$ and h* are defined with respect to the slot coordinate system $x_{s,i}$, $y_{s,i}$, $z_{s,i}$. Because bracket translation occurs parallel to the $y_{b,i}$ axis of the bracket base coordinate system, bracket translation distance is defined as ($h_i$–h*)/cosine (α).

FIG. 4C shows a simplified view of FIG. 4B that illustrates the geometric components used to determine the bracket translation distance ($h_i$–h*)/cosine (α). Similarly, FIG. 4D reduces FIG. 4C to a right triangle having acute angle α and legs $h_i$–h*, ($h_i$–h*) tan α, and ($h_i$–h*)/cosine (α).

Occlusal height control module 24 defines the bracket translation axis (118) as the intersection of the bracket slot plane ($x_{s,i}$, $y_{s,i}$) and the bracket base plane ($y_{b,i}$, $z_{b,i}$). Next, occlusal height control module translates the bracket along bracket translation axis by the bracket translation distance ($h_i$–h*)/cosine (α) (120).

Figure 5A:
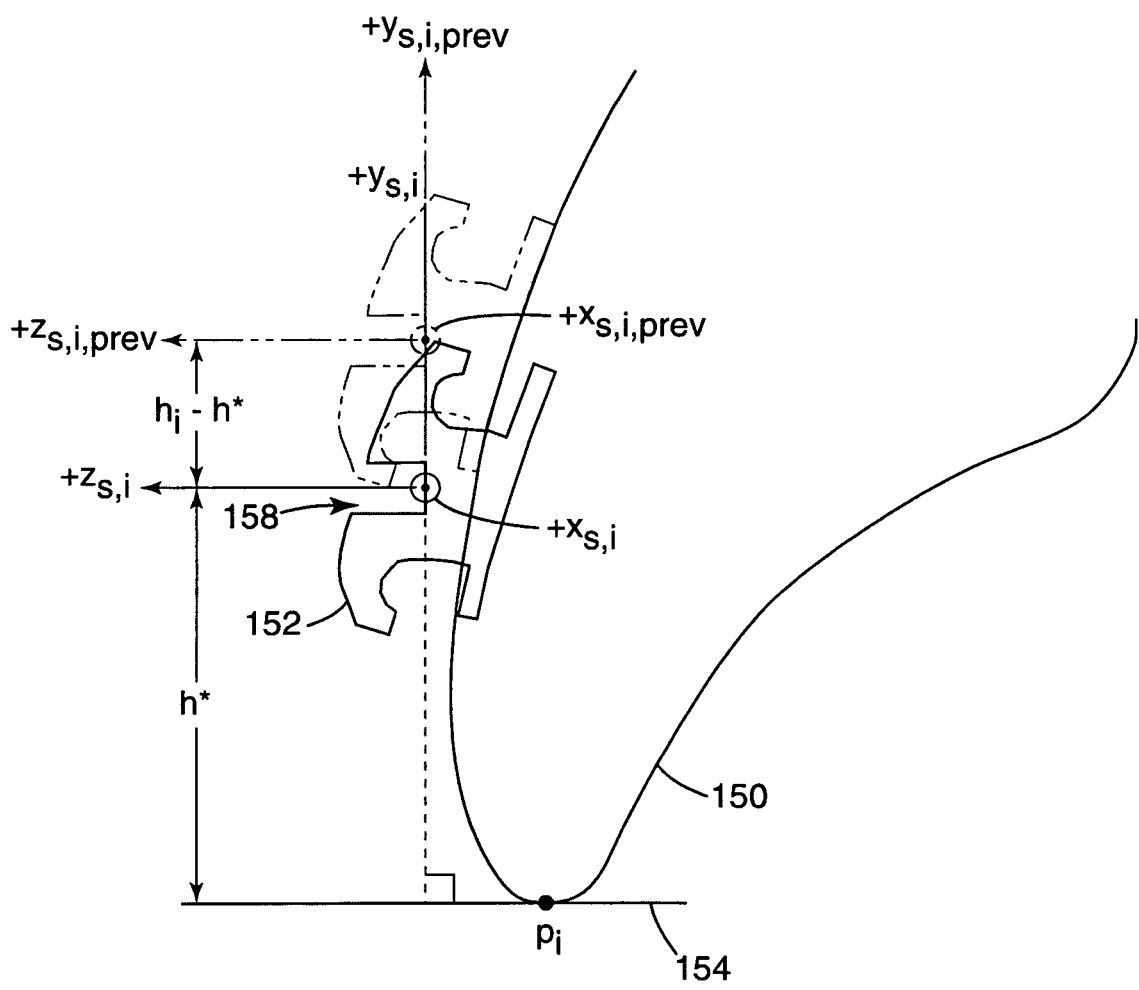
FIGS. 5A-5C are diagrams illustrating translation of an orthodontic bracket on an anterior tooth.

FIG. 5A shows the resulting translated bracket 152 and the previous location of the bracket in phantom line. FIG. 5A shows a mid-sagittal cross section of the anterior tooth 150 of FIGS. 4A and 4B with an orthodontic bracket 152 that has been translated along the bracket translation axis by a distance of ($h_i$–h*)/cosine (α) from its previous position (shown in phantom line). Again, this translation distance corresponds to a distance of $h_i$–h* in the mid-sagittal plane when projected thereon. The previous bracket position (from FIG. 4A) and bracket slot coordinate system ($x_{s,i,prev}$, $y_{s,i,prev}$, $z_{s,i,prev}$) are shown in phantom line.

Figure 5B:
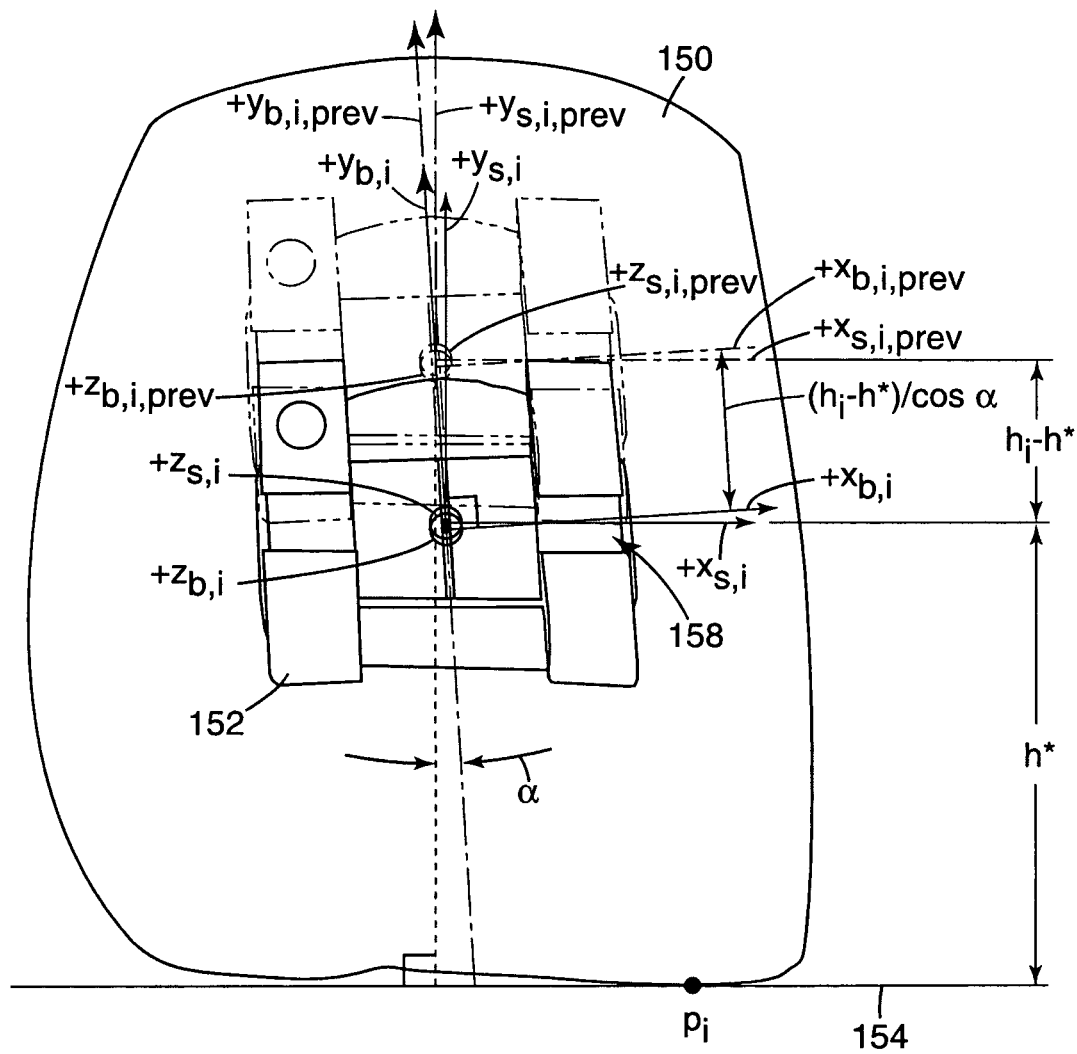

FIG. 5B shows a facial view of anterior tooth 150 of FIG. 5A after translation of bracket 152. Shown is bracket base coordinate system ($x_{b,i}$, $y_{b,i}$, $z_{b,i}$), bracket slot coordinate system ($x_{s,i}$, $y_{s,i}$, $z_{s,i}$), occlusal-most point $p_i$ relative to this coordinate system, desired occlusal height h*, $h_i$–h*, bracket angulation α, and bracket translation distance ($h_i$–h*)/cosine (α). The previous bracket position (the position shown in FIG. 5A), previous bracket base coordinate system ($x_{b,i,prev}$, $y_{b,i,prev}$, $z_{b,i,prev}$), and previous bracket slot coordinate system ($x_{s,i,prev}$, $y_{s,i,prev}$, $z_{s,i,prev}$) are shown in phantom line.

Figure 5C:
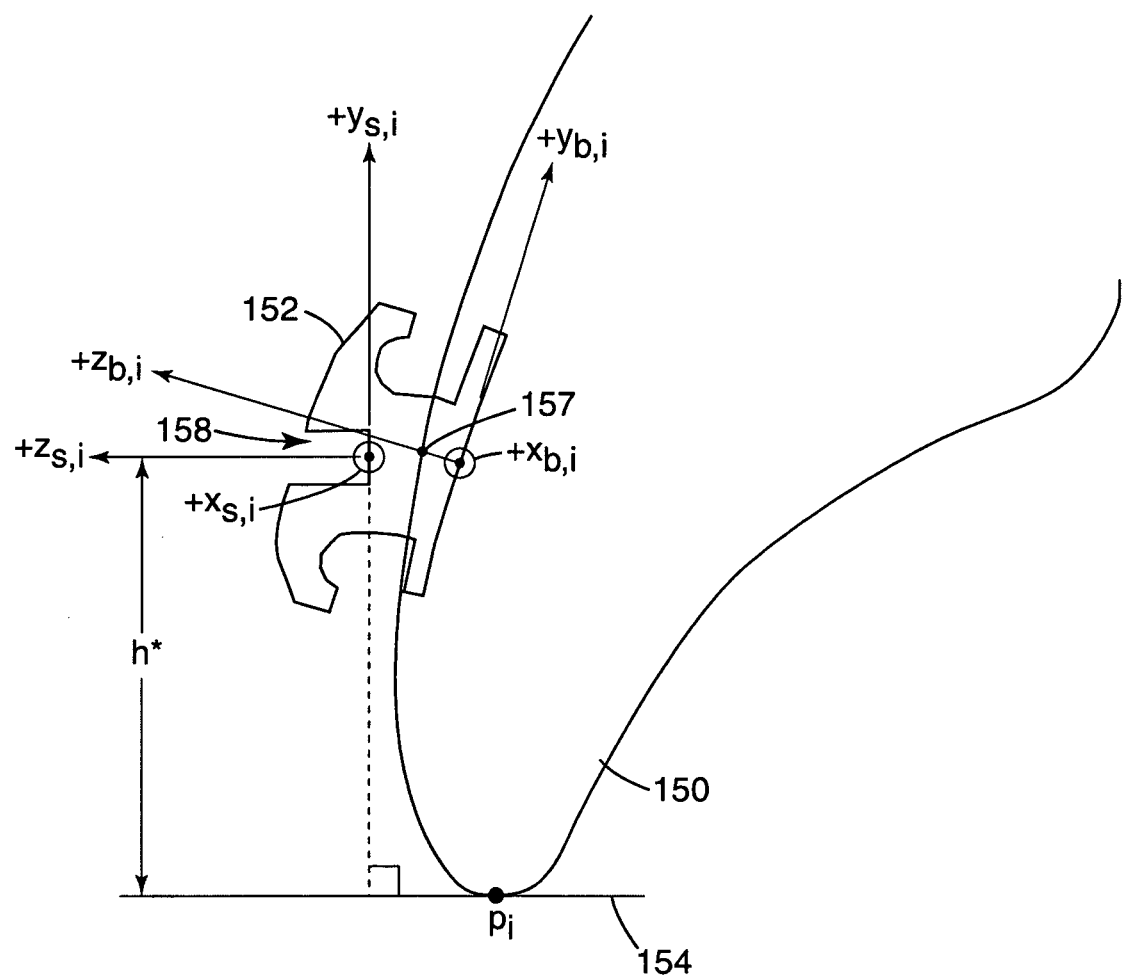

FIG. 5C shows a mid-sagittal cross section of the anterior tooth 150 of FIGS. 5A and 5B with a translated orthodontic bracket 152 that is now positioned at the desired occlusal height h* but whose base is no longer fitted to the surface of tooth 150. The labio-lingual axis $z_{b,i}$ of the bracket base coordinate system intersects the facial surface of tooth 150 at point 157, which will be the approximate new location of the origin of the base coordinate system. Occlusal height control module 24 refits the bracket on the tooth to attain an optimized fit between the base of the bracket and the tooth surface (122). One way to achieve this is to refit the bracket to achieve a close mating fit between the bracket and the tooth surface using the method described in U.S. patent application Ser. No. 10/734,323, substituting axis $z_{b,i}$ for the line of sight.

Figure 6:
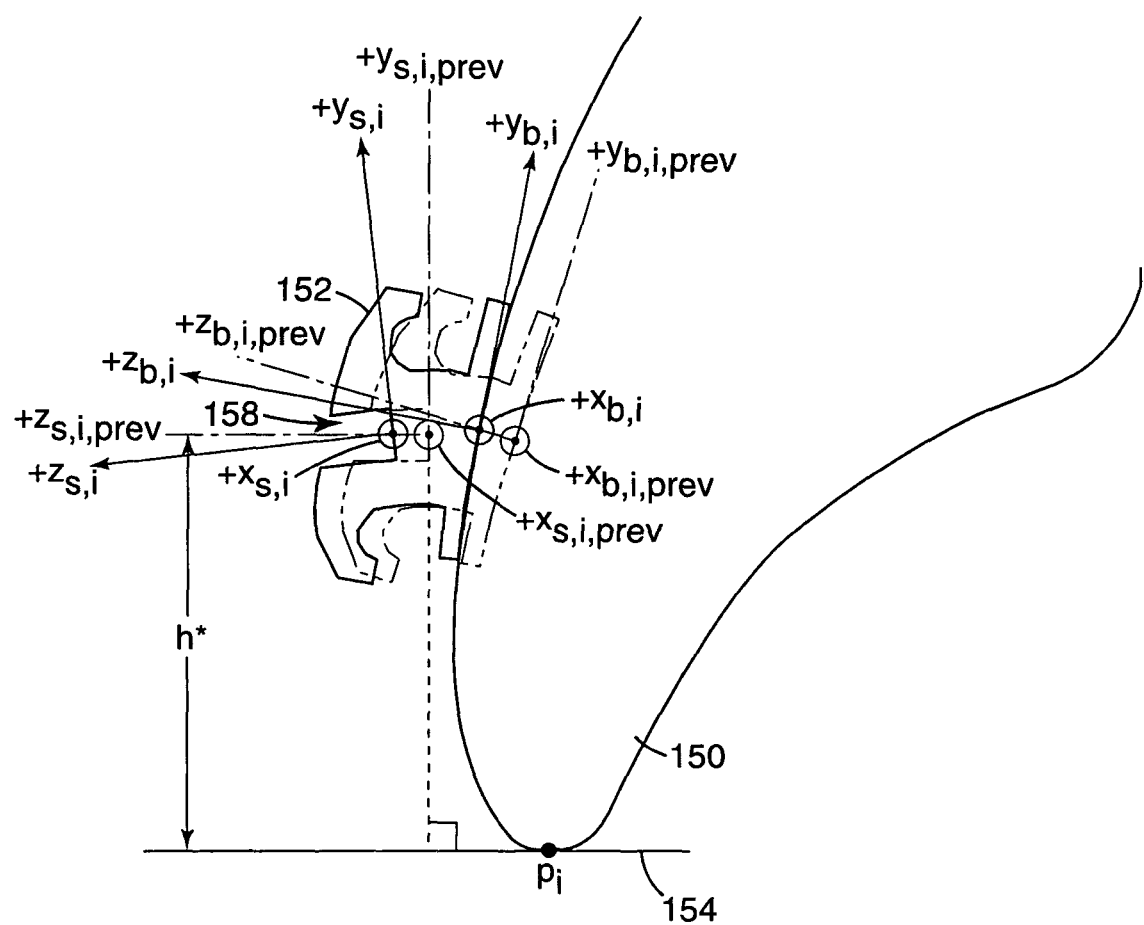
FIG. 6 is a diagram illustrating the refitting of an orthodontic bracket on a tooth.

FIG. 6 shows a mid-sagittal cross section of an anterior tooth 150 with orthodontic bracket 152 with the base refitted to tooth 150 as a result of the refitting (122). The previous position of the bracket (the position of FIG. 5B), the previous bracket base coordinate system ($x_{b,i,prev}$, $y_{b,i,prev}$, $z_{b,i,prev}$), and previous bracket slot coordinate system ($x_{s,i,prev}$, $y_{s,i,prev}$, $z_{s,i,prev}$) are shown in phantom line.

Figure 7:
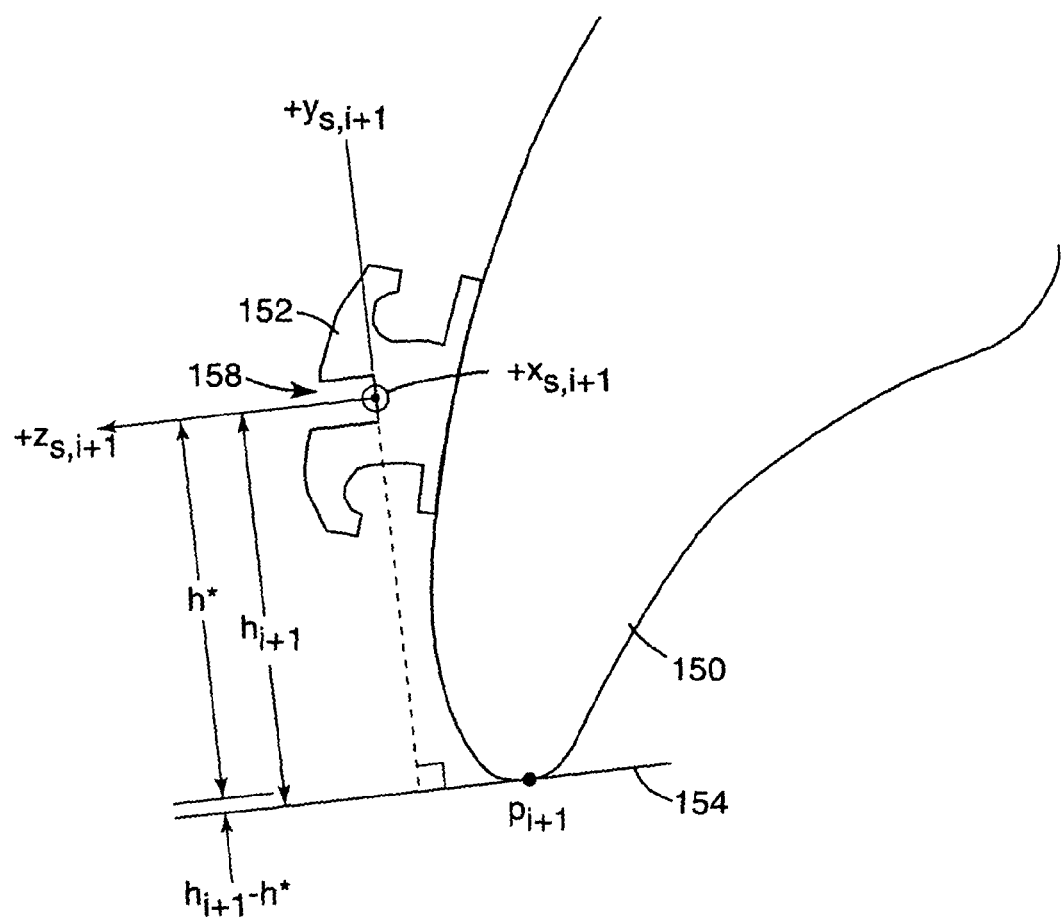
FIG. 7 illustrates a mid-sagittal cross section of an anterior tooth with an orthodontic bracket and the bracket base coordinate system indicating completion of a full iteration.

FIG. 7 shows a mid-sagittal cross section of tooth 150 at the beginning of the next iteration (i+1). As shown, after bracket translation the bracket slot coordinate system ($x_{s,i+1}$, $y_{s,i+1}$, $z_{s,i+1}$) for the next iteration (i+1) translates along with the bracket based on the new bracket position. Also shown in FIG. 7 are the occlusal-most point $p_{i+1}$ relative to this coordinate system, current occlusal height $h_{i+1}$, desired occlusal height h*, and $h_{i+1}$–h*. Note that in FIG. 7 bracket 152 has not changed position or orientation from FIG. 6, rather, the nomenclature has changed to indicate the completion of a full iteration (e.g. i→i+1).

FIG. 7 also illustrates that refitting bracket 152 may affect the orientation of the current occlusal height $h_i$ such that it is no longer approximates the value of (or falls within the allowable error ϵ of) the desired occlusal height h*. The automatic bracket adjustment process therefore continues with a series of iterations, translating and refitting bracket 152 until the actual occlusal height $h_i$ of bracket 152 falls within the error ϵ of the desired occlusal height h*. Occlusal height control module 24 increments the iteration number i (124) and repeats the process to determine the occlusal most point $p_{i+1}$ (110) and the current occlusal height $h_{i+1}$ (112) for the next iteration (e.g., iteration i+1).

Although the method described above refers to determining the current and desired occlusal height of a bracket with respect to the occlusal-most point $p_i$ on a particular tooth, occlusal height control module 24 may use any of a number of other quantities to determine occlusal height of a bracket. For example, in another embodiment, instead of determining occlusal height of the bracket with respect to the occlusal-most point $p_i$ on the tooth, occlusal height control module 24 may determine occlusal height of the bracket with respect to an average of a defined number of occlusal-most points on the tooth. The method of FIGS. 3A and 3B may then use this average occlusal-most point to determine occlusal height of the bracket. For example, occlusal height control module 24 may determine the position of a defined number of occlusal-most points on a tooth (e.g., the number of cusps on a multi-cusp tooth, such as the four cusps of a molar), calculate an average occlusal-most point, $p_{i,avg}$, and determine occlusal height of the bracket with respect to that average, $p_{i,avg}$.

In another embodiment, occlusal height control module may determine a best fit plane through a defined number of occlusal-most points on a tooth, and determine occlusal height of the bracket with respect to that occlusal-most plane of the tooth. For example, occlusal height control module 24 may determine the position of a defined number of occlusal-most points on a tooth (e.g., the number of cusps on a multi-cusp tooth, such as the four cusps of a molar, or a defined number of the occlusal-most points on any tooth, regardless of whether it is multi-cusp), calculate a best fit occlusal-most plane, and determine occlusal height of the bracket with respect to that best fit occlusal-most plane.

In another embodiment, occlusal height control module may determine occlusal height of the bracket with respect to an occlusal-most point of the dental arch in which the tooth is one of a plurality of teeth. In yet another embodiment, occlusal height control module may determine occlusal height of the bracket with respect to an occlusal-most plane of the dental arch. It shall be understood, therefore, that the invention is not limited concerning the point with respect to which occlusal height of the bracket is determined, and that many different points and/or planes associated with an individual tooth, with multiple teeth, or with the entire dental arch may be used by the occlusal height control module to determine occlusal height of the bracket.

Figure 8:
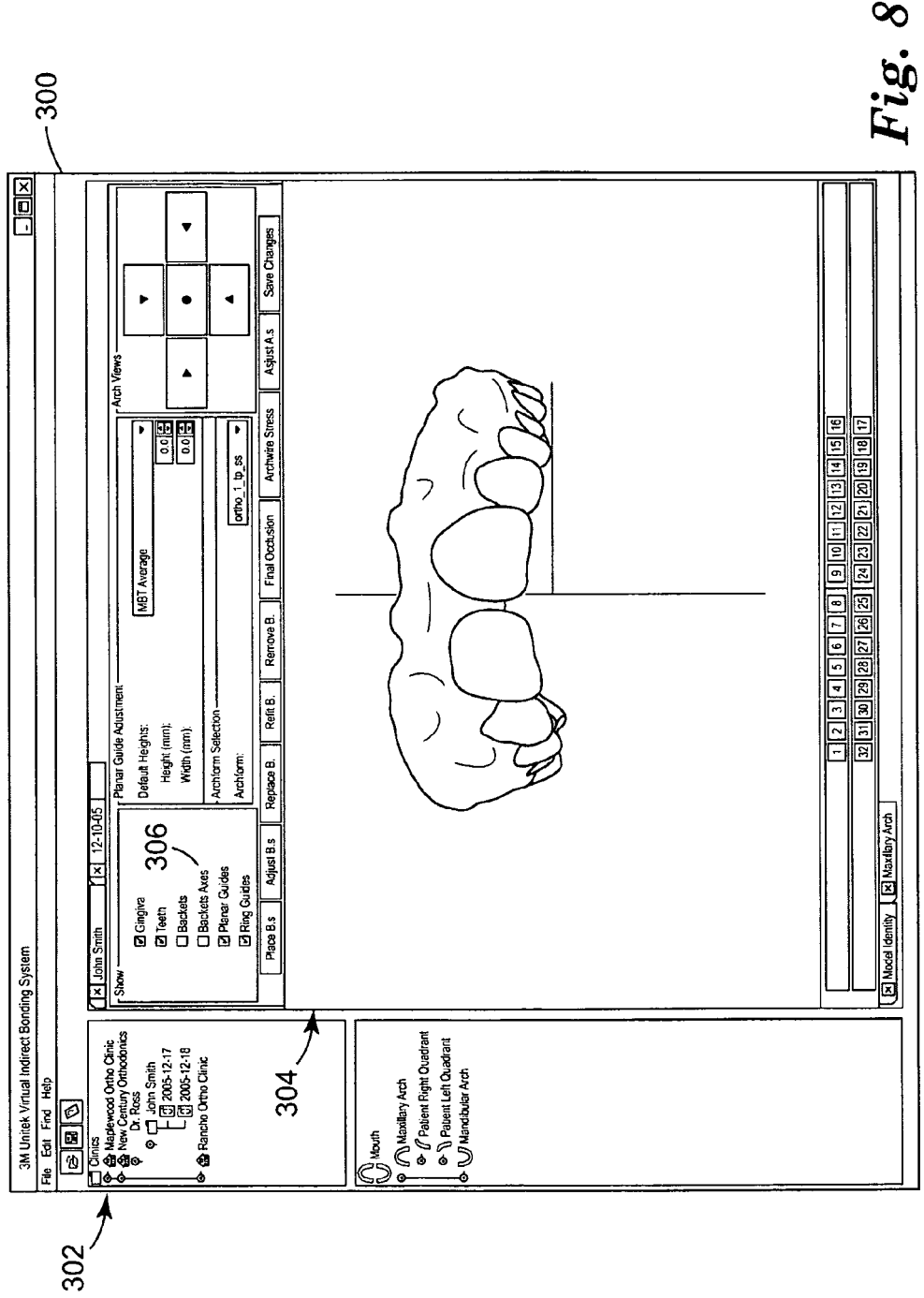
FIGS. 8, 9 and 10 are display diagrams of an example user interface presented by the system for automatic orthodontic bracket adjustment.

FIG. 8 is a display diagram illustrating exemplary graphical user interfaces (GUIs) presented by modeling software 20. For example, FIG. 8 illustrates an exemplary user interface 300. In the illustrated embodiment, user interface 300 includes a menu input area 302 by which a user, e.g., practitioner 8, accesses an electronic prescription for patient 6.

User interface 300 further includes display area 304 for presenting the 3D rendered representation of the teeth of patient 6. In this example, display area 304 presents a virtualized facial view of the malocclusal dental arch of patient 6. User interface 300 provides selection mechanism 306 by which practitioner 8 can selectively enable and disable the rendering and display of any of several different views of the patient's dental arch within the display area 302.

Figure 9:
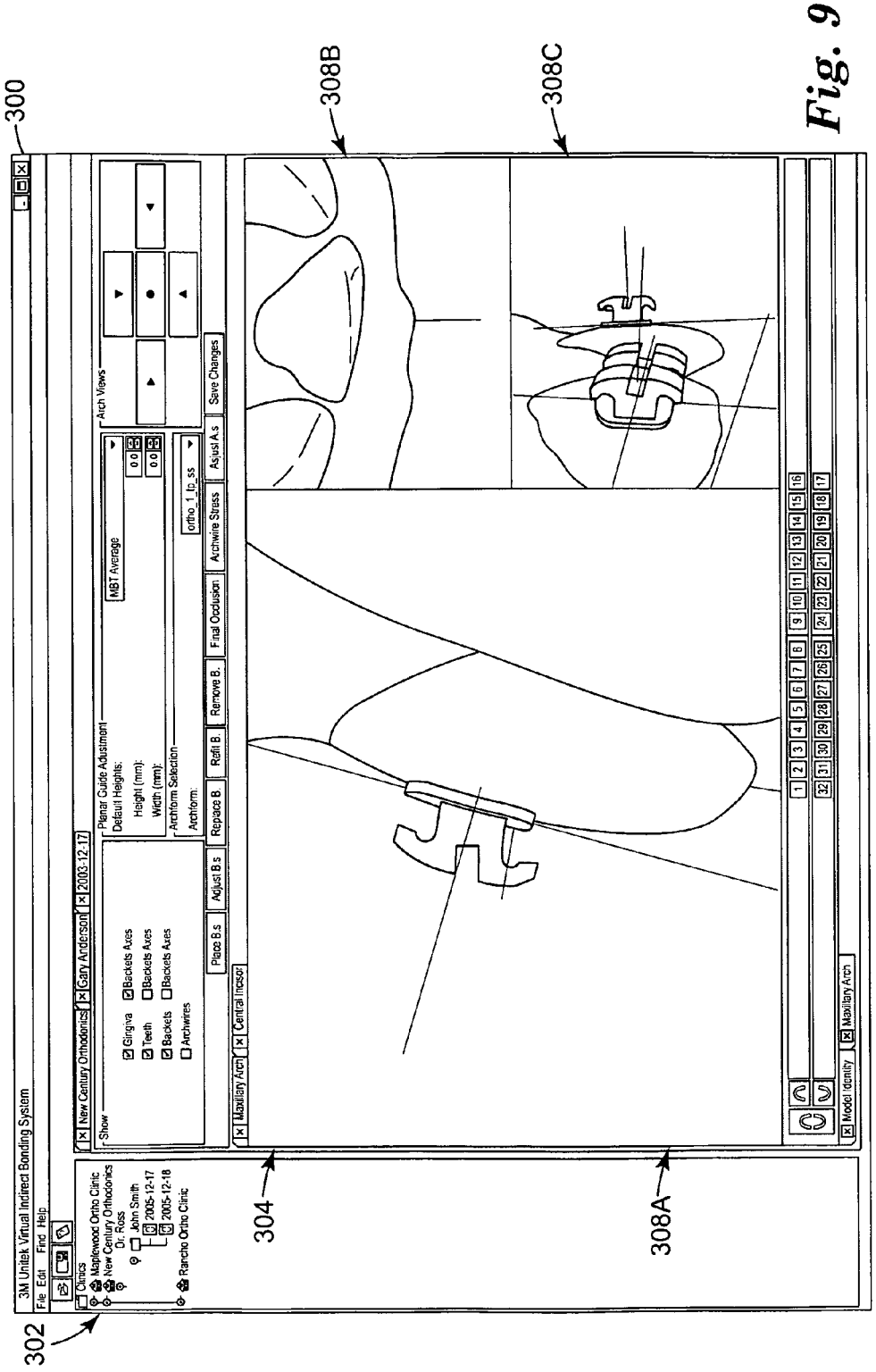

FIG. 9 illustrates an exemplary embodiment in which modeling software 20 places display area 302 into a bracket view mode having three viewing regions 308A, 308B and 308C. In this example, a bracket 152 is positioned on tooth 150 within the malocclusal dental arch. Viewing region 308A provides an expanded oblique view of the tooth 150, while viewing region 308A provides a zoomed or "close-up" view of tooth 150. Viewing region 308B provides an occlusal view of tooth 150. The bracket position and orientation shown in viewing regions 308A, 308B and 308C of FIG. 9 are analogous to the position and orientation of bracket 152 as shown in FIGS. 4A and 4B.

Figure 10:
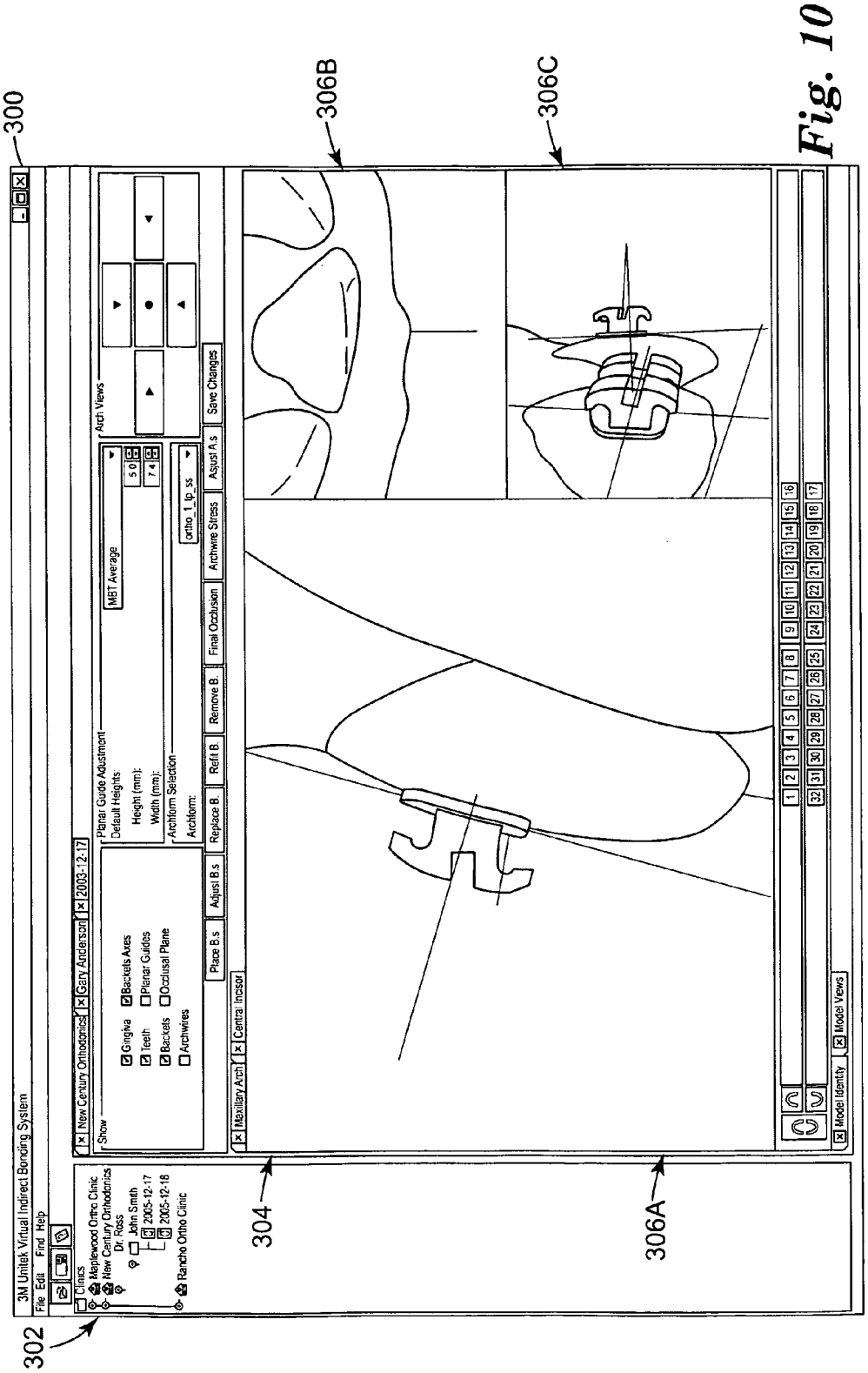

FIG. 10 illustrates an exemplary embodiment showing display area 302 in bracket view mode after one iterative translation and refitting of bracket 152. The bracket position and orientation shown in viewing regions 308A, 308B and 308C are analogous to the position and orientation of bracket 152 as shown in FIG. 7.

Figure 11A:
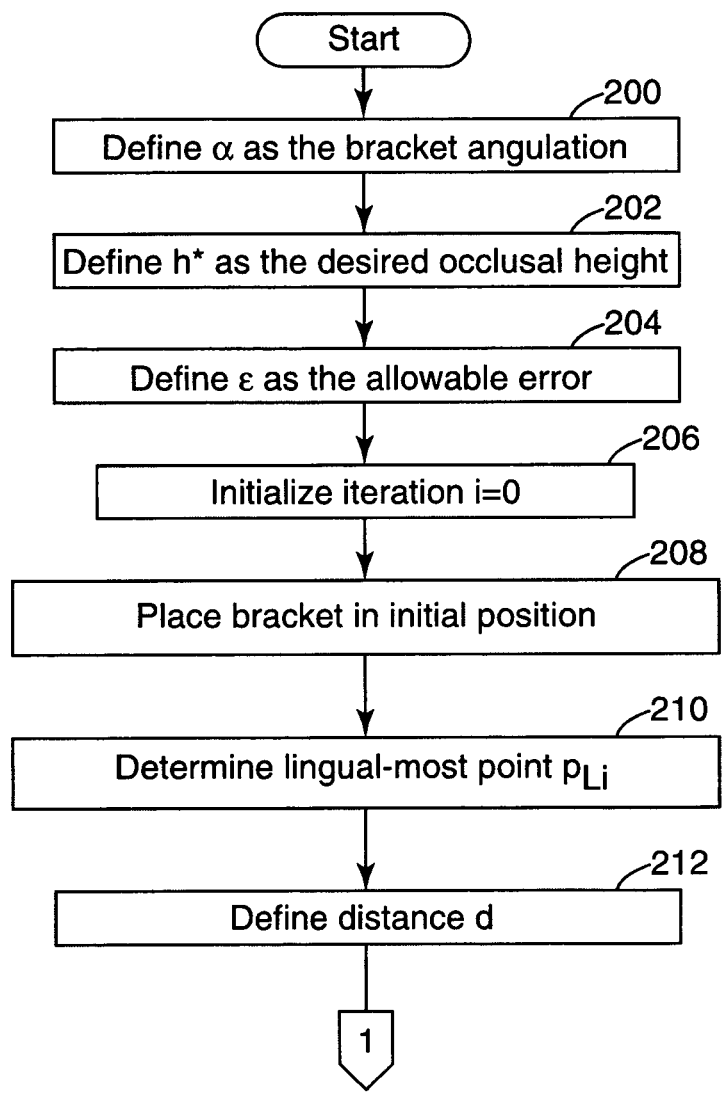
FIGS. 11A-11C are a flowchart illustrating an example embodiment of a method of automatic orthodontic bracket adjustment on a multi-cusp tooth.
Figure 11B:
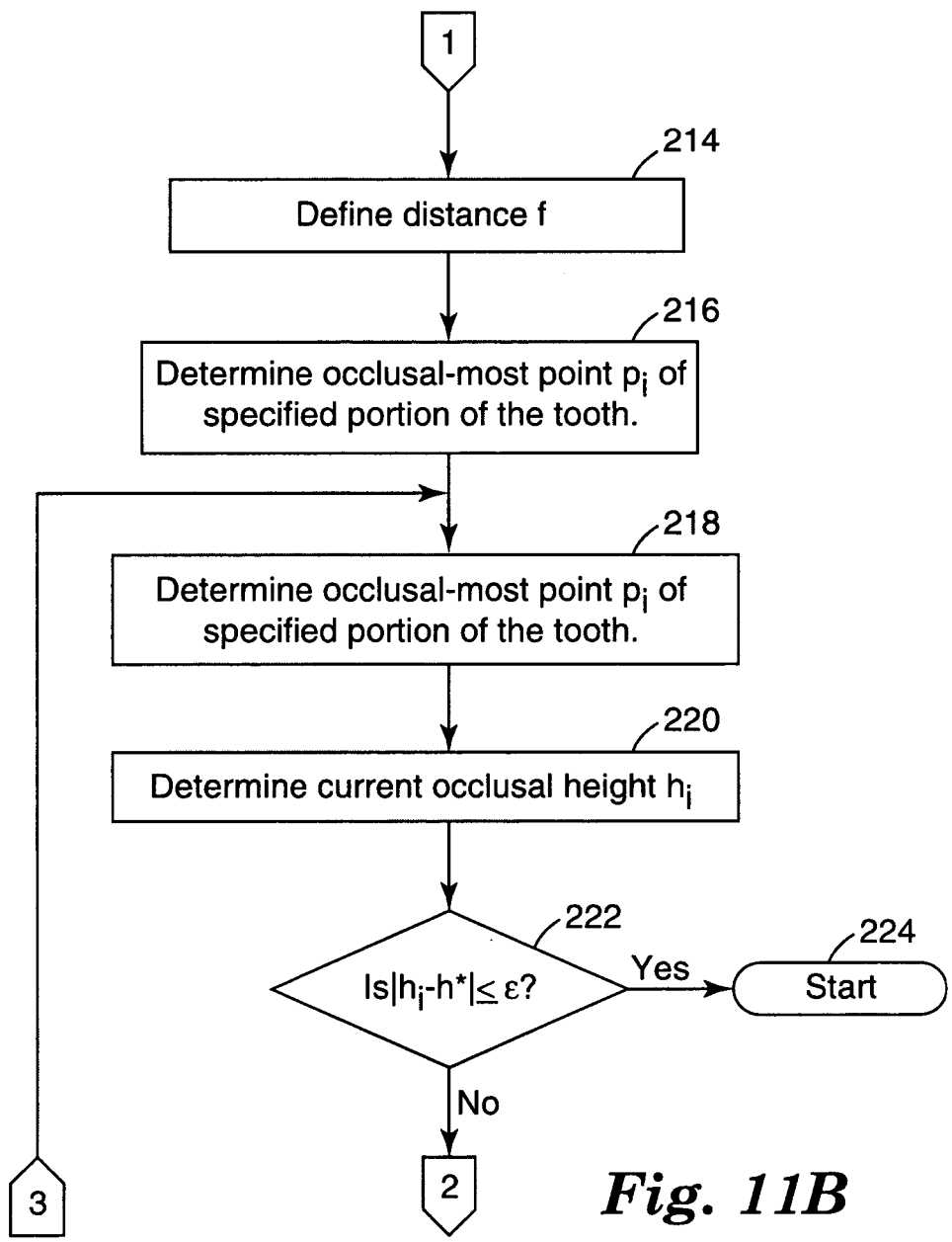
Figure 11C:
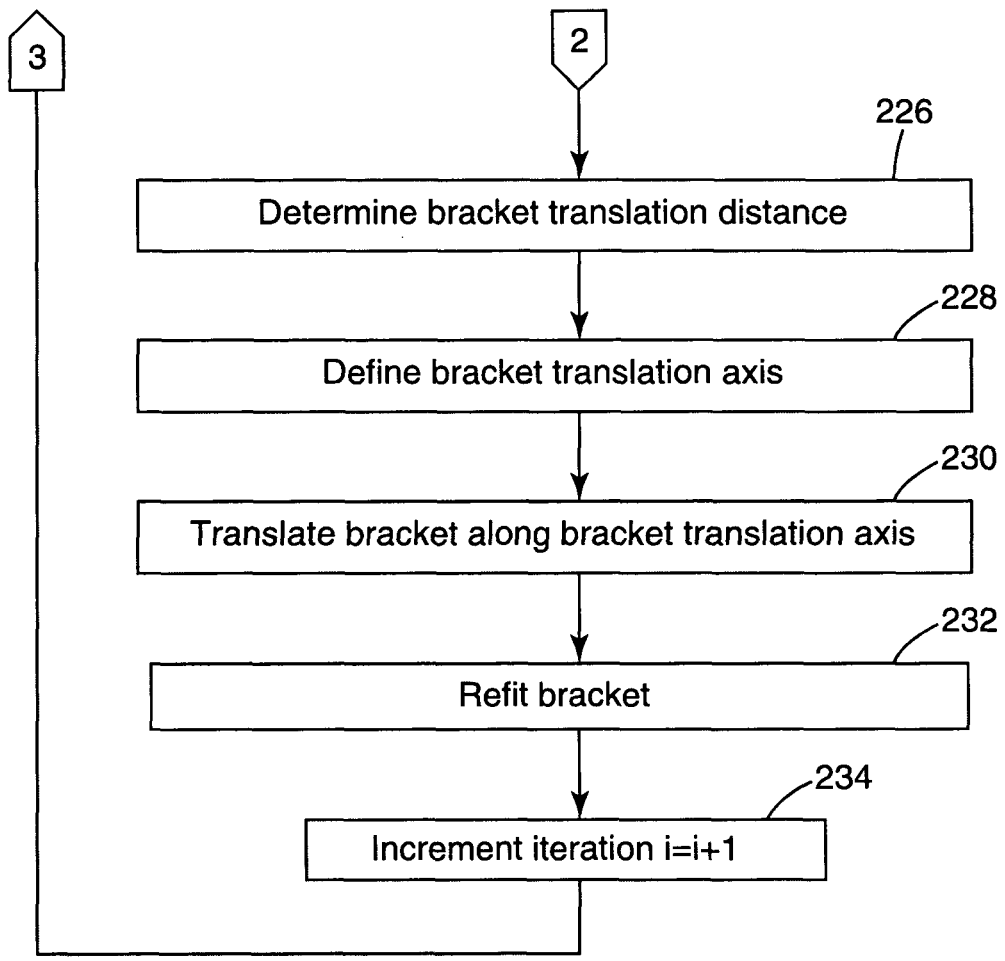

FIGS. 11A, 11B and 11C are a flowchart illustrating another method of automatically adjusting orthodontic brackets. More specifically, the flowchart of FIGS. 11A, 11B and 11C illustrates another exemplary mode of operation of occlusal height control module 24 in automatically adjusting orthodontic brackets within the 3D virtual environment. The method shown in FIGS. 11A, 11B and 11C may be used on anterior teeth (incisor or cuspid) as well as on posterior teeth (bicuspid or molar). The method shown in FIGS. 11A, 11B and 11C will be described with respect to a multi-cusp tooth, such as that commonly encountered with posterior teeth (bi-cuspids or molars).

Figure 12:
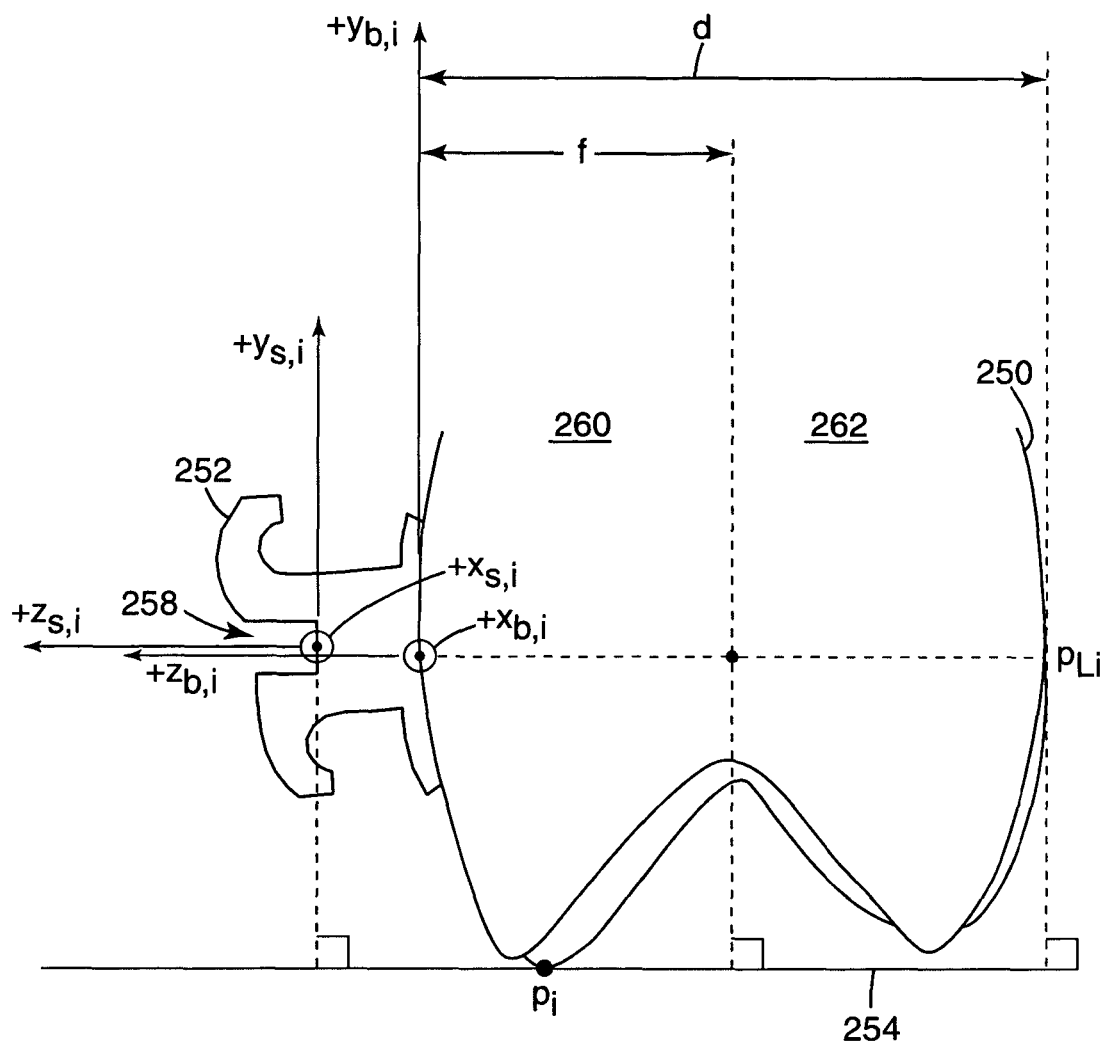
FIG. 12 is a mid-sagittal cross section of a multi-cusp tooth sectioned into a labial portion and a lingual portion.

As with the embodiment shown in FIG. 3A, the embodiment of automatic orthodontic bracket adjustment shown in FIG. 12 begins by defining the bracket angulation $\alpha$ (200), the desired occlusal height h* (202) and the allowable error $\epsilon$ between the current occlusal height $h_i$ and the desired occlusal height h* (204). The iteration quantity i is initialized to zero on the first iteration through the process (206).

Next, modeling software 20 places a bracket in an initial position on the facial surface of one of the teeth within the modeled dental arch (208). In one embodiment, the bracket is positioned such that axis $y_{b,0}$ of bracket base coordinate system $(x_{b,0}, y_{b,0}, z_{b,0})$ aligns with the FACC of tooth 150. Modeling software 20 may accomplish this using the method described in the above-referenced copending and commonly assigned U.S. patent application Ser. No. 10/734,323. Again, this method places a bracket on a tooth to attain a close, mating fit between the base of the bracket and the tooth surface.

Next, occlusal height control module 24 sections the tooth into two portions, a labial portion (the side facing the patient's lips or cheeks) and a lingual portion (the side facing the patient's tongue). FIG. 12 illustrates a mid-sagittal cross section of a multi-cusp tooth 250 with an orthodontic bracket 252 whose base is in contact with tooth 250. The multi-cusp tooth 250 is sectioned into a labial portion 260 and a lingual portion 262. Also shown is the bracket slot coordinate system $(x_{s,i}, y_{s,i}, z_{s,i})$ in its original position in the center of slot 258.

Referring again to FIG. 11A, to section the tooth, modeling software 20 determines the lingual-most point $p_{Li}$ of tooth 250 (210). This lingual-most point $p_{Li}$ is determined relative to the bracket slot coordinate system $(x_{s,i}, y_{s,i}, z_{s,i})$ translated to the bracket base origin. The bracket base origin is defined as the point that lies at the center of the bracket base. The translated bracket slot coordinate system is represented by axes $x_{s',i}, y_{s',i}$, and $z_{s',i}$ (see FIG. 12).

Occlusal height control module 24 determines distance d (212). Distance d is defined relative to the bracket base coordinate system $(x_{b,i}, y_{b,i}, z_{b,i})$ as the distance in the lingual direction (i.e., along the $z_{b,i}$ axis) from the bracket base origin to the lingual-most point $p_{Li}$ of tooth 250. Occlusal height control module 24 determines a "sectioning distance" f (214) as a value used to section the tooth into two portions, labial portion 260 and lingual portion 262. The sectioning distance f may be defined as any value between 0<f<d. In one embodiment, the sectioning distance f may be chosen as approximately one half the distance d. In another embodiment, the sectioning distance f is chosen such that labial portion 260 does not include any lingual-side cusps.

Next, occlusal height control module 24 determines the occlusal-most point $p_i$ of the labial portion 260 of the tooth relative to the bracket slot coordinate system ($x_{s,i}$, $y_{s,i}$, $z_{s,i}$) (216). To do this, occlusal height control module 24 restricts the search for the occlusal-most point $p_i$ to all points on the tooth whose distance from the bracket base origin in the lingual direction relative to the bracket slot coordinate system is less than or equal to the sectioning distance f. Occlusal height control module 24 uses this occlusal-most point $p_i$ in automatically adjusting a bracket to the desired occlusal height.

Figure 13A:
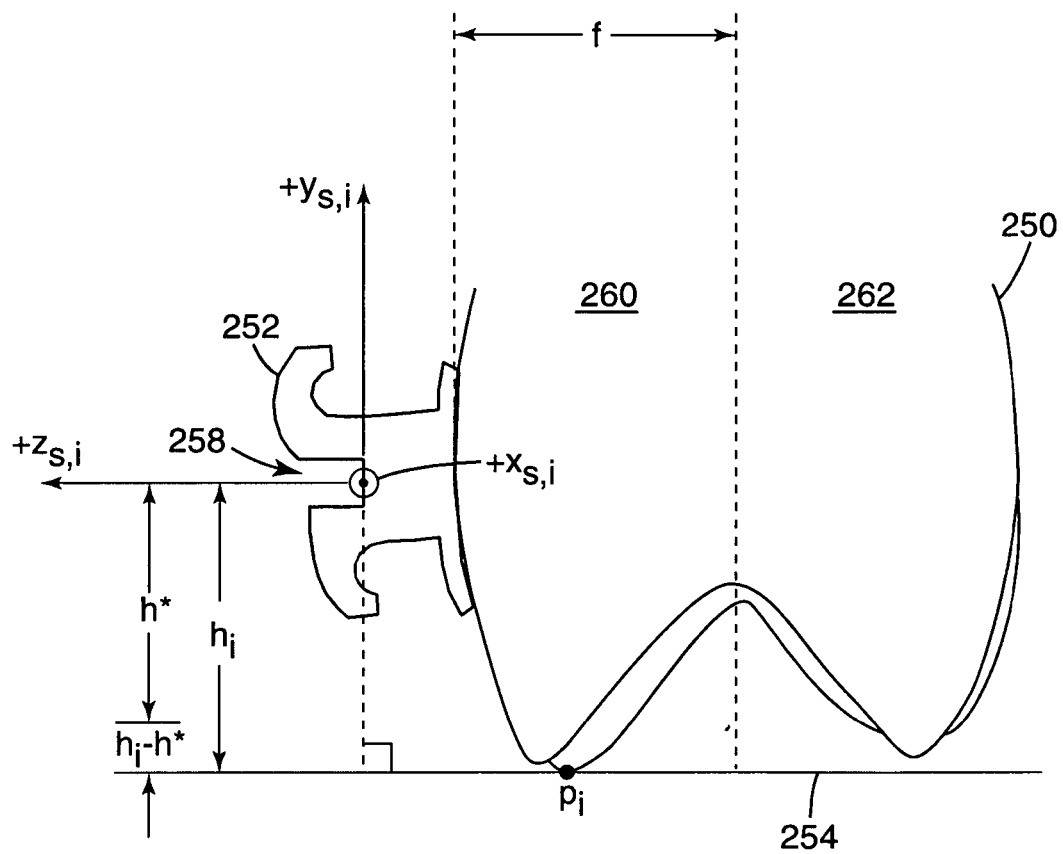
FIGS. 13A-13D and 14A-B illustrate translation of an orthodontic bracket on a multi-cusp tooth according to the method shown in FIGS. 11A-C.

FIG. 13A shows a mid-sagittal cross-section of a multi-cusp tooth with an orthodontic bracket whose base is in optimal contact with the tooth. Indicated is the bracket position and orientation at iteration i, after completion of step 216 in the flowchart of FIG. 11B. Shown are bracket slot coordinate system ($x_{s,i}$, $y_{s,i}$, $z_{s,i}$), occlusal-most point $p_i$ relative to this coordinate system, current occlusal height $h_i$, desired occlusal height h*, and $h_i-h$*.

Occlusal height control module 24 next automatically adjusts the bracket to the desired occlusal height, h*, in a manner similar to that described above with respect to FIGS. 3A and 3B. Occlusal height control module 24 determines the occlusal-most point $p_i$ of the labial portion of the tooth relative to the bracket slot coordinate system ($x_{s,i}$, $y_{s,i}$, $z_{s,i}$) (218). Occlusal height control module 24 next determines the current occlusal height $h_i$ based on the occlusal most point $p_i$ (220). If the current occlusal height is within the specified error $\epsilon$ of the desired occlusal height (222), the desired occlusal height has been achieved, the bracket need not be adjusted any further and the process finishes (224).

If the current occlusal height is not within the specified error $\epsilon$ of the desired occlusal height (222), modeling software 20 determines the bracket translation distance $(h_i-h^*)/\cos(\alpha)$ (226). The bracket translation axis is defined as the intersection of the bracket slot plane ($x_{s,i}$, $y_{s,i}$) and the bracket base plane ($y_{s,i}$, $z_{s,i}$) (228). Occlusal height control module 24 then translates the bracket along the bracket translation axis by the distance $(h_i-h^*)/\cos(\alpha)$ (230).

Figure 13B:
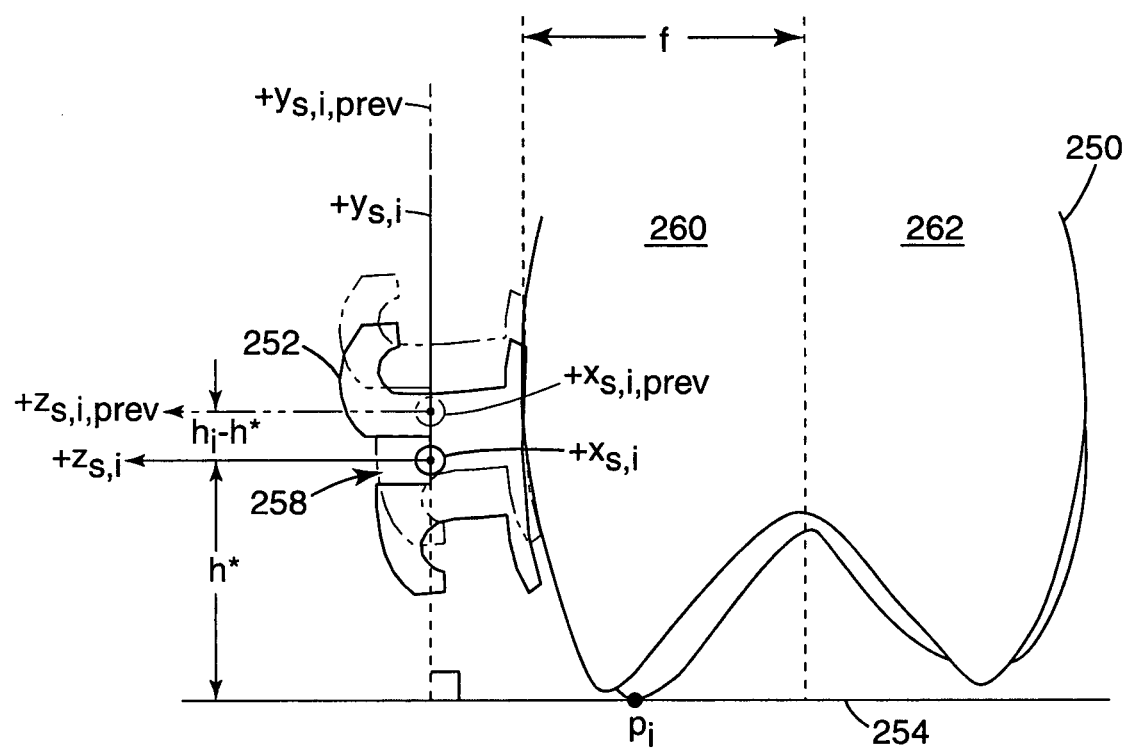

FIG. 13B shows a mid-sagittal cross-section of a multi-cusp tooth with an orthodontic bracket that has been translated along the bracket translation axis by a distance of $(h_i-h^*)/\cos(\alpha)$, which corresponds to a distance of $h_i-h$* in the mid-sagittal plane when projected thereon. Shown is bracket slot coordinate system ($x_{s,i}$, $y_{s,i}$, $z_{s,i}$), occlusal-most point $p_i$ relative to this coordinate system, desired occlusal height h*, and $h_i-h$*. The previous bracket position from FIG. 13A and previous bracket slot coordinate system ($x_{s,i,prev}$, $y_{s,i,prev}$, $z_{s,i,prev}$) are shown in phantom line.

Figure 13C:
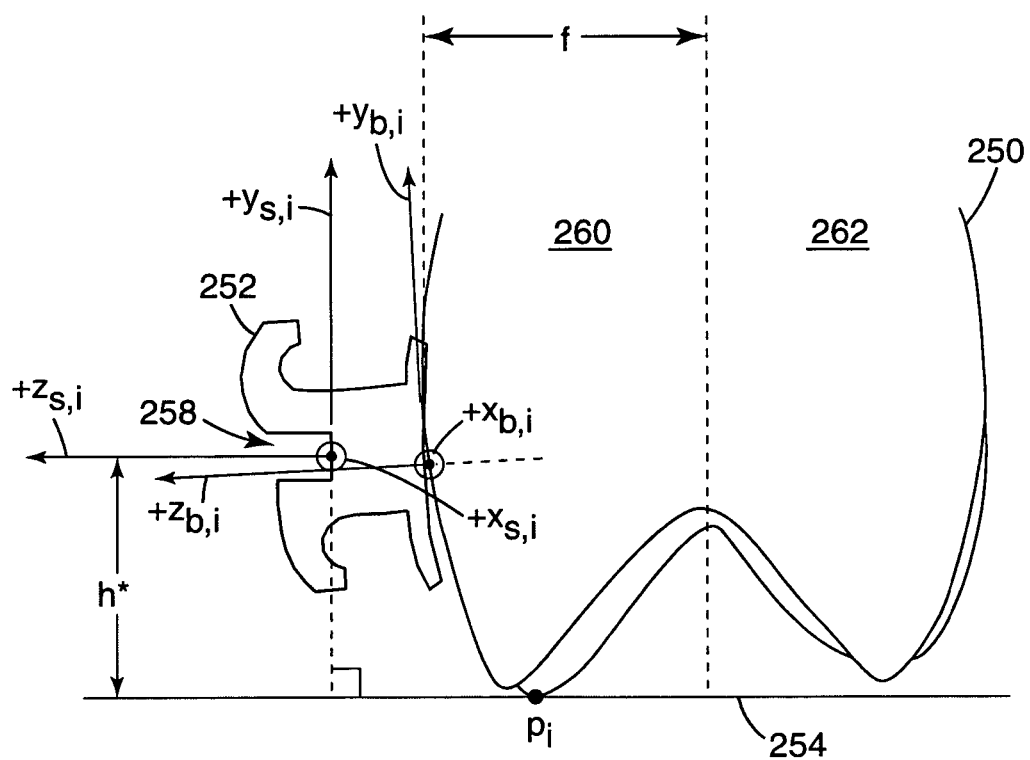

FIG. 13C shows a mid-sagittal cross-section of a multi-cusp tooth with an orthodontic bracket that is now positioned at the desired occlusal height h* but whose base is not necessarily in optimal contact with the tooth. Shown is bracket base coordinate system ($x_{b,i}$, $y_{b,i}$, $z_{b,i}$), bracket slot coordinate system ($x_{s,i}$, $y_{s,i}$, $z_{s,i}$), occlusal-most point $p_i$ relative to this coordinate system, desired occlusal height h*, and the point at which the labio-lingual axis, $z_{b,i}$, of the bracket base coordinate system intersects the facial surface of the tooth.

Occlusal height control module 24 next refits the bracket for optimized contact with the tooth (232). To accomplish this, occlusal height control module 24 may refit the bracket to achieve a close, mating fit between the bracket and the tooth surface using the method described in the above-referenced U.S. patent application Ser. No. 10/734,323, substituting axis $z_{b,i}$ for the line of sight. Finally, the iteration number is incremented in preparation for the next iteration (234).

Figure 13D:
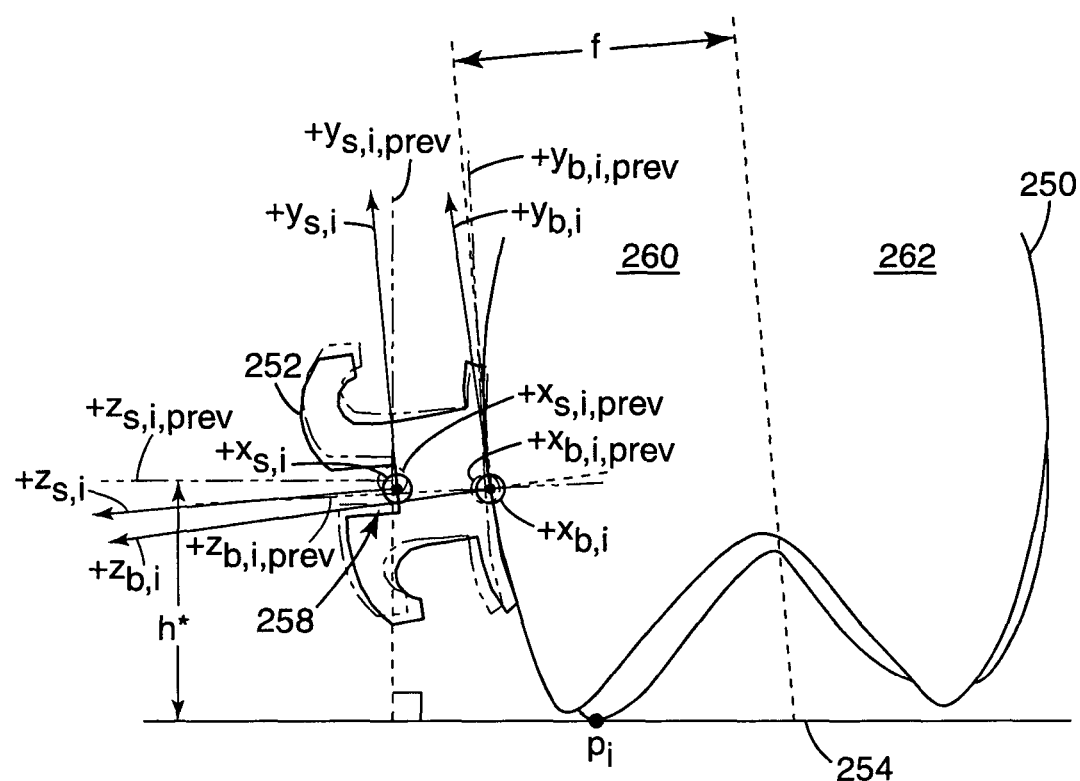

FIG. 13D shows a mid-sagittal cross-section of a multi-cusp tooth with an orthodontic bracket that was previously positioned at the desired occlusal height h* but whose base is now in optimal contact with the tooth after refitting. Shown is bracket base coordinate system ($x_{b,i}$, $y_{b,i}$, $z_{b,i}$), bracket slot coordinate system ($x_{s,i}$, $y_{s,i}$, $z_{s,i}$), occlusal-most point $p_i$ relative to this coordinate system, and desired occlusal height h*. The previous bracket position from FIG. 13C, previous bracket base coordinate system ($x_{b,i,prev}$, $y_{b,i,prev}$, $z_{b,i,prev}$), and previous bracket slot coordinate system ($x_{s,i,prev}$, $y_{s,i,prev}$, $z_{s,i,prev}$) are shown in phantom line.

Figure 14A:
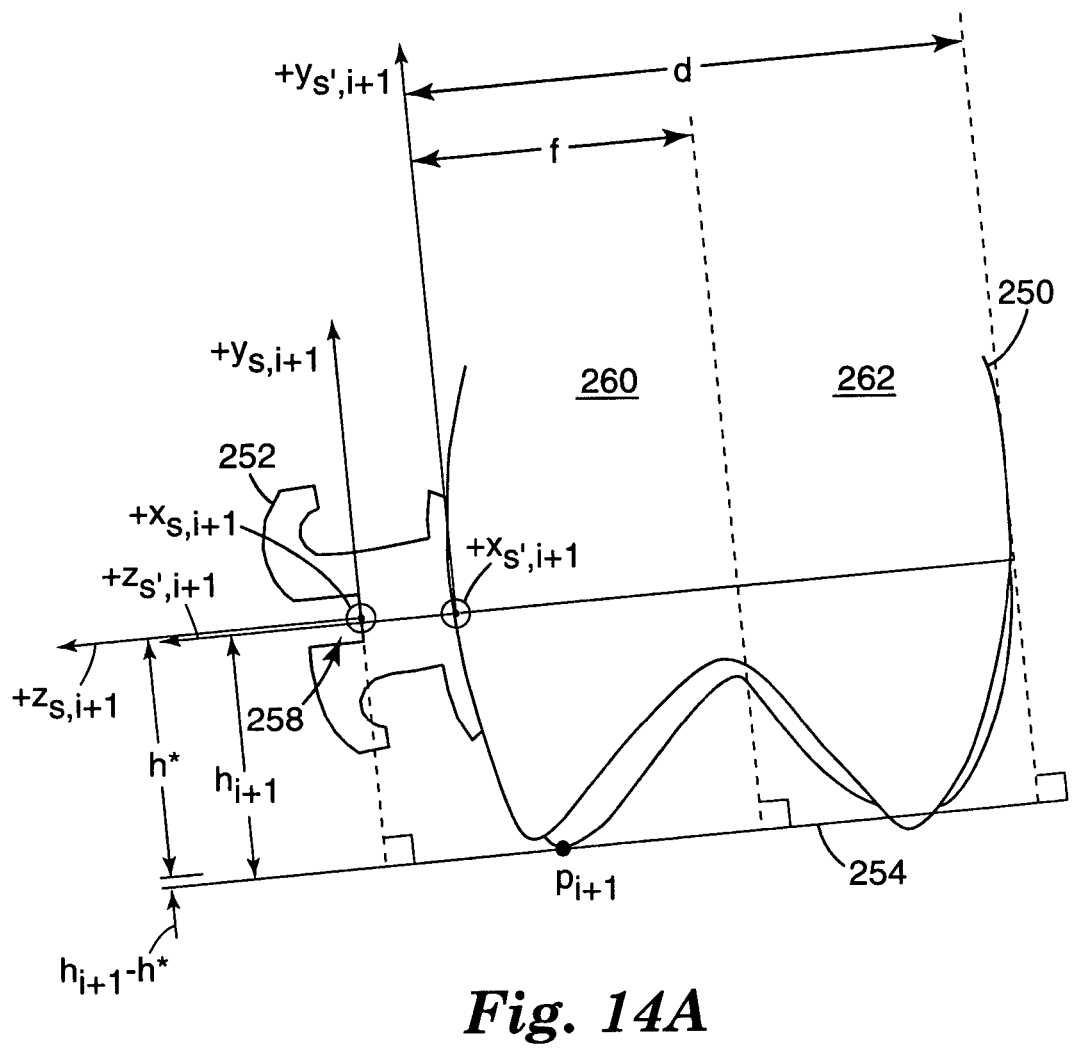

FIG. 14A illustrates a mid-sagittal cross-section of a multi-cusp tooth with an orthodontic bracket whose base is in optimal contact with the tooth. As illustrates, the refitting of the bracket for optimal contact with the tooth has affected achievement of the desired occlusal height. FIG. 14A shows the bracket slot coordinate system ($x_{s,i+1}$, $y_{s,i+1}$, $z_{s,i+1}$) for this iteration (i+1) in its position in the center of the slot. The same bracket slot coordinate system is also shown translated to the bracket base origin ($x_{s',i+1}$, $y_{s',i+1}$, $z_{s',i+1}$). Distance d is shown to be the maximum distance along the translated bracket slot coordinate system's $-z_{s,i+1}$ axis where some point on the tooth projects. Distance f is a value in the range 0<f<d used section the tooth into two portions, a labial portion 260 and a lingual portion 262. FIG. 14A also shows occlusal-most point $p_{i+1}$ relative to the bracket slot coordinate system and lying in the labial portion of the tooth.

Figure 14B:
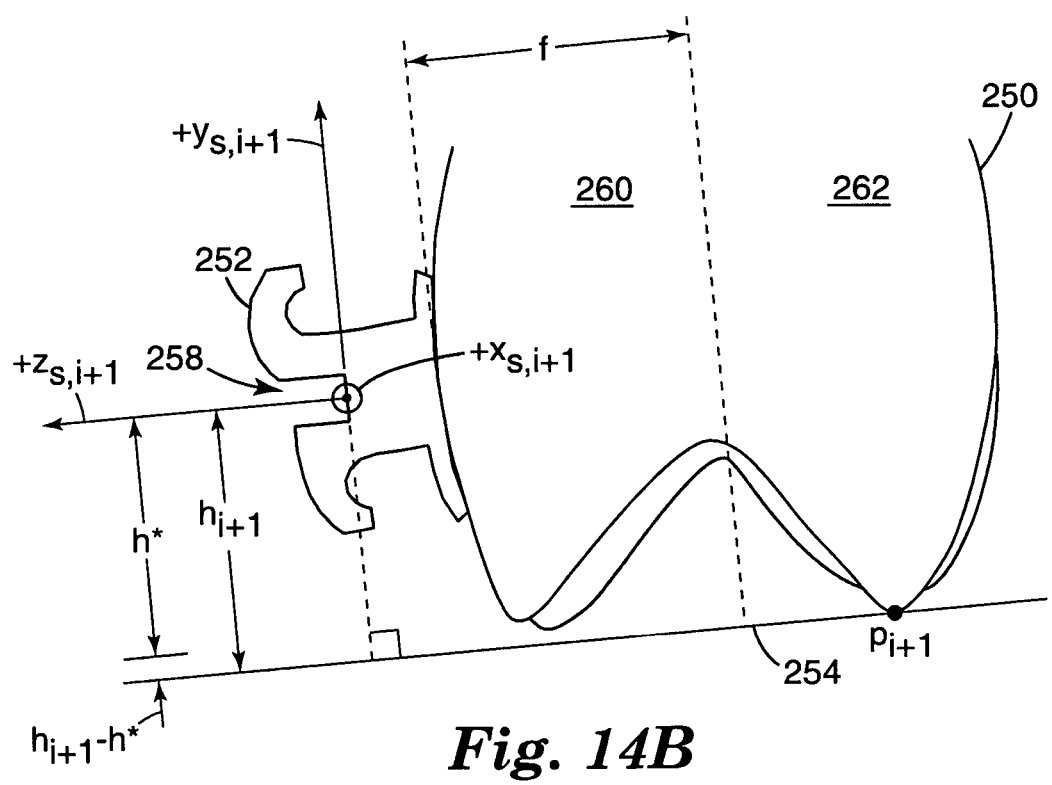
Figure 15A:
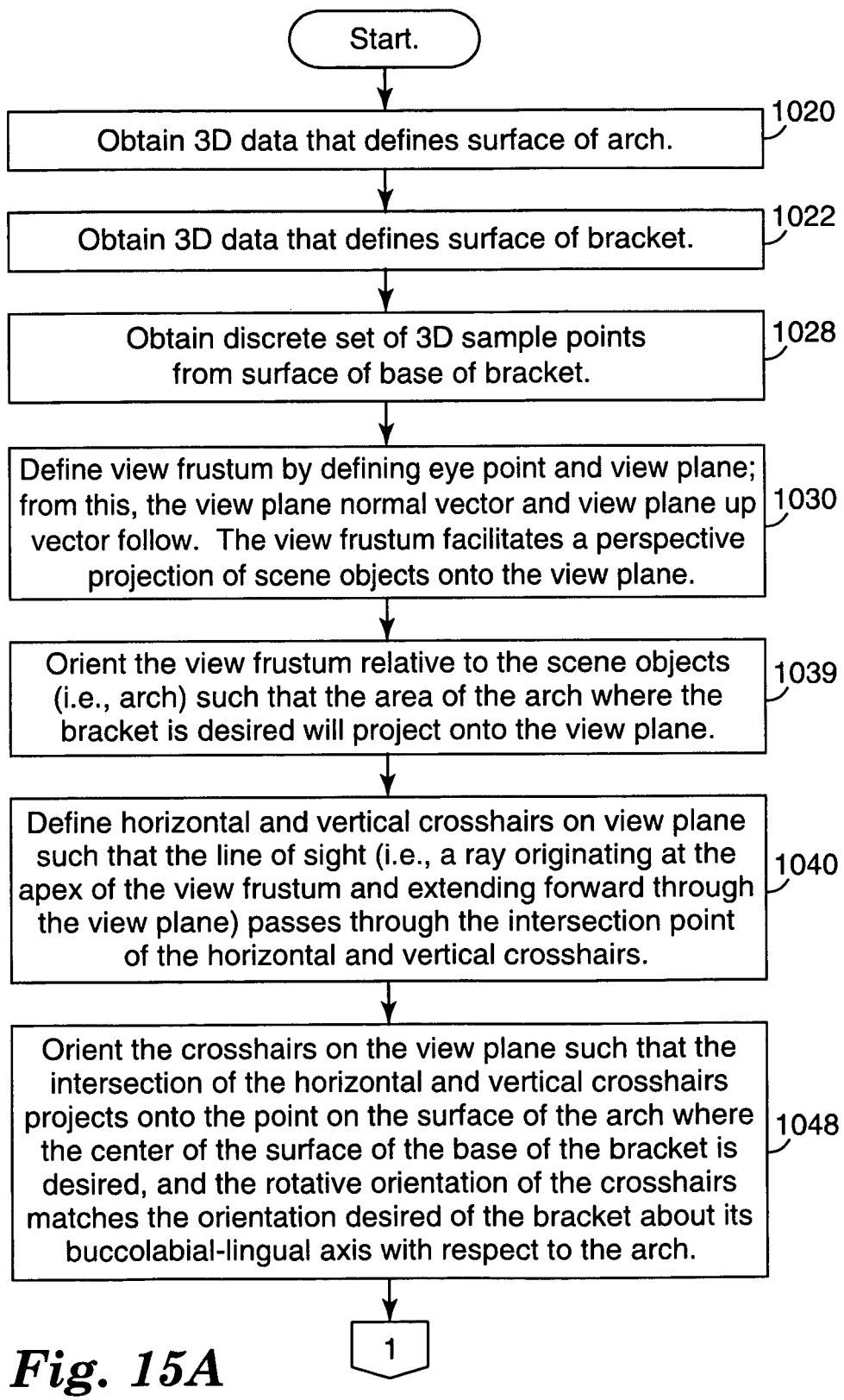
FIGS. 15A-15E collectively depict a flow chart describing a method of selecting a relative orientation of an orthodontic appliance and a tooth according to one embodiment of the present invention.
Figure 15B:
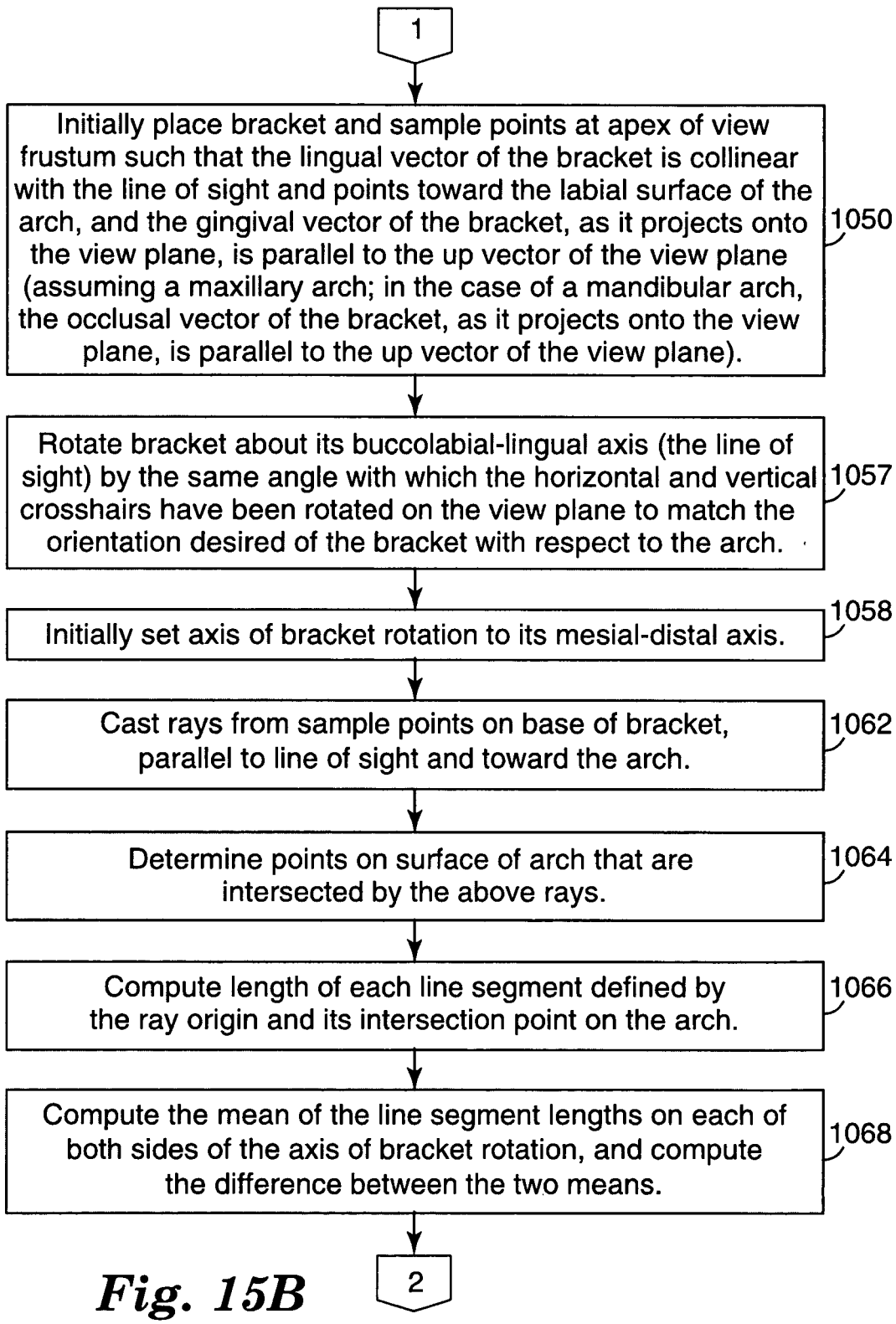
Figure 15C:
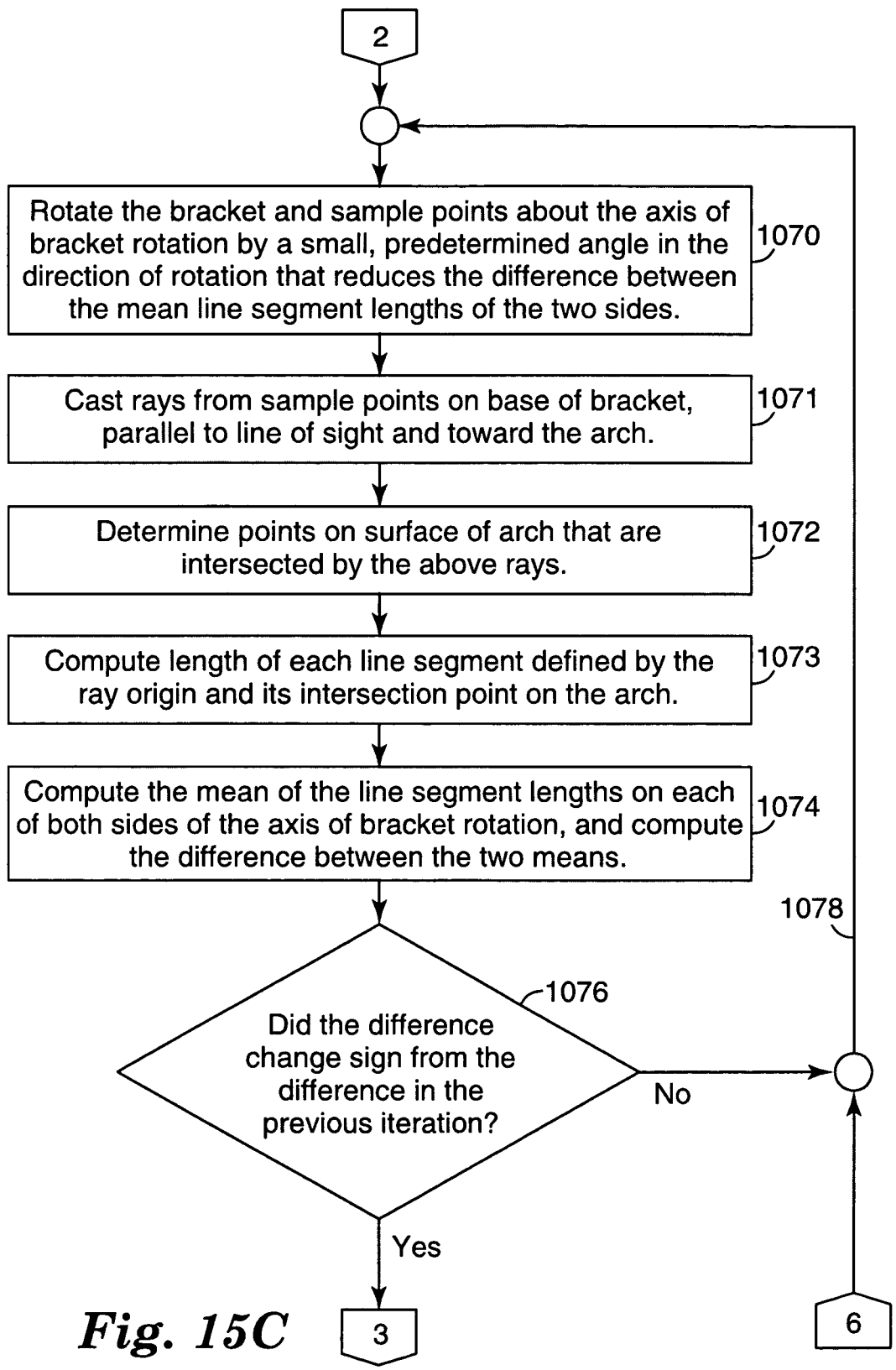
Figure 15D:
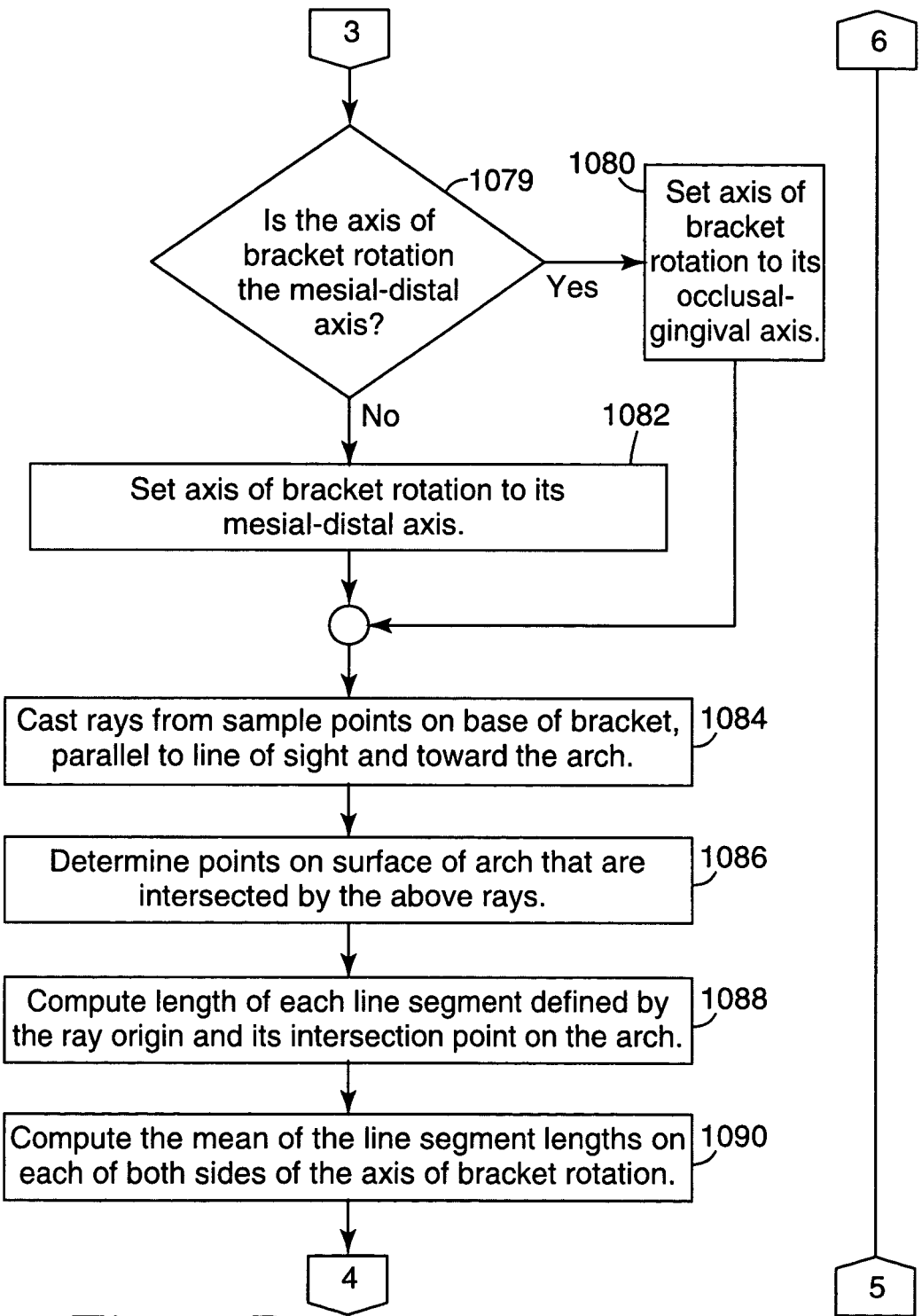
Figure 15E:
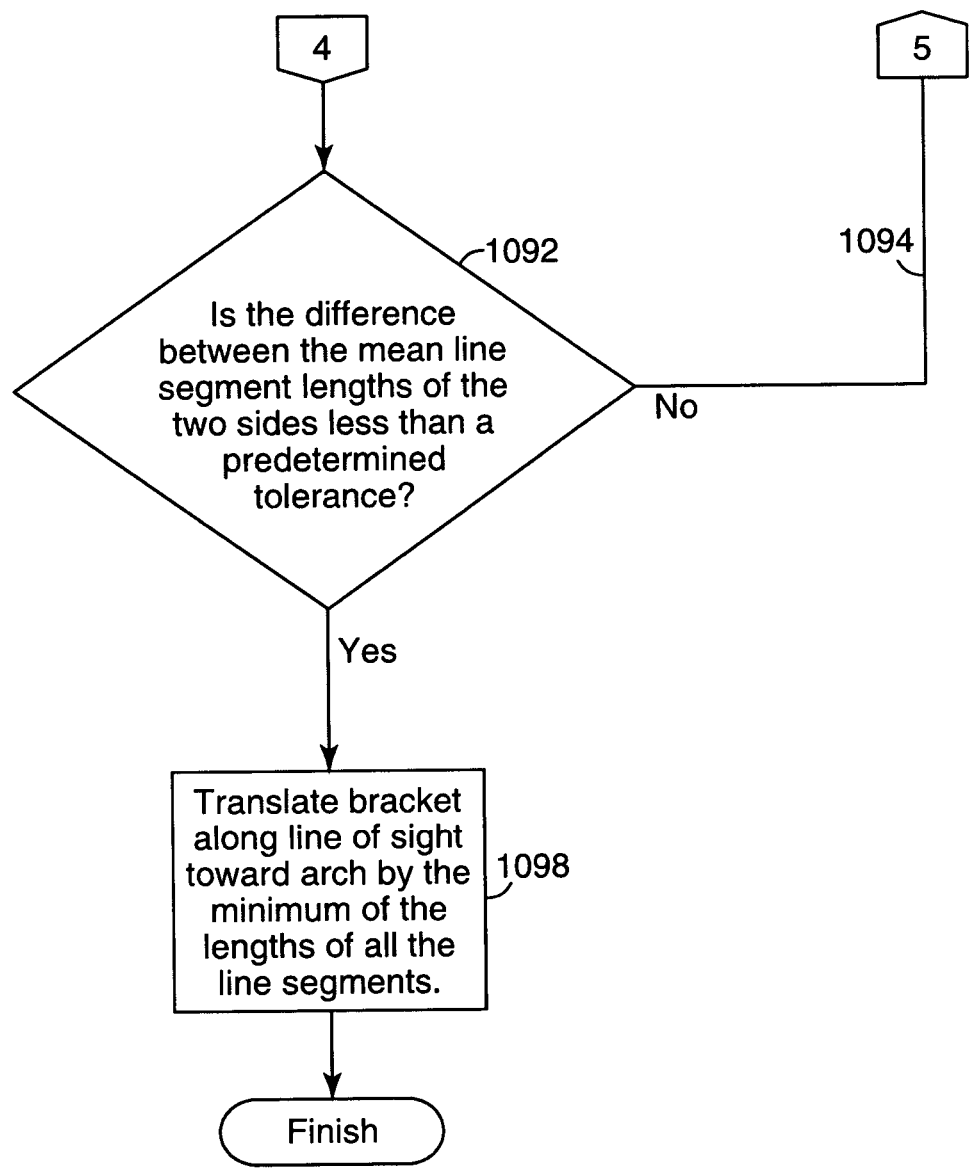

FIG. 14B shows a mid-sagittal cross-section of a multi-cusp tooth of FIG. 14A showing the bracket slot coordinate system ($x_{s,i+1}$, $y_{s,i+1}$, $z_{s,i+1}$) for the next iteration (i+1). Also shown are the occlusal-most point $p_{i+1}$ relative to this coordinate system, current occlusal height $h_{i+1}$, desired height h*, and $h_{i+1}-h$*. Note that in this figure, the bracket and its coordinate systems have not changed position or orientation from FIG. 14A, rather, the nomenclature has changed to indicate the completion of a full iteration.

The automatic bracket adjustment process of FIGS. 11A-C continues with a series of iterations, translating and refitting bracket 252 until the actual occlusal height $h_i$ of bracket 252 falls within the error $\epsilon$ of the desired occlusal height h*. Occlusal height control module 24 returns to determine the occlusal most point $p_{i+1}$ (218) and the current occlusal height $h_{i+1}$ (220) for the next iteration (e.g., iteration i+1).

In another embodiment, occlusal height control module 24 may use the occlusal-most point on the lingual portion of the tooth 262 instead of labial portion of the tooth 260 (see FIG. 12). This embodiment may be useful when placing brackets on the lingual side of the tooth, or when the practitioner wants to measure the desired occlusal height with respect to a lingual-side cusp.

FIGS. 15-28 illustrate one example embodiment of how occlusal height control module 24 may initially place (108 in FIG. 3A, or 208 in FIG. 11A) a bracket on a tooth and/or refit a bracket on a tooth after the tooth has been translated to attain a fit between the base of the bracket and the tooth surface (122 in FIG. 3B or 232 in FIG. 11C). FIGS. 15-28 illustrate the method described in the above-referenced U.S. patent application Ser. No. 10/734,323. When using this method to initially place a bracket or to refit a bracket, occlusal height control module 24 substitutes axis $z_{b,i}$ for the line of sight referred to in the following discussion. It shall be understood, however, that the invention is not limited in this respect, and that other techniques may be used without departing from the scope of the present invention.

FIG. 15 is a block diagram showing various acts of a method for selecting a relative orientation of an orthodontic appliance on a orthodontic patient's tooth according to one embodiment of the invention. The method is particularly advantageous when used as a computer program. However, certain acts set out in the block diagram may be carried out manually if desired.

The method described in FIG. 15 includes the act in Block 1020 of obtaining three-dimensional data that defines a surface of a dental arch. The surface of the dental arch may include all of the teeth of the upper or lower dental arch, or only some of the teeth of the upper or lower arch. Preferably, the surface includes all exposed sections of the dental arch with all of the sides of each tooth including the buccolabial side (i.e., the side facing the patient's lips or cheeks), the lingual side (i.e., the side facing the patient's tongue), the occlusal side (i.e., the side extending along the outer tip of each tooth), the mesial side (i.e., the side facing the middle of the patient's dental arch) and the distal side (i.e., the side facing away from the middle of the patient's dental arch). However, one or more sides of the teeth may be omitted if desired.

The data obtained in Block 1020 may be obtained by any suitable means known in the art. For example, data representative of the teeth may be created by using a scanner such as an intra-oral camera that is held in the patient's oral cavity, or an X-ray apparatus or other type of radiation apparatus. Alternatively, a set of digital data may be obtained by the use of a contact probe that engages the surface of the patient's dental arch at a multitude of locations.

As another alternative, the data representative of the patient's teeth may be obtained by first taking an impression of the patient's teeth using a curable impression material. Next, digital data is obtained by scanning the impression with a camera or other device, or by use of the apparatus described in PCT Publication No. WO97/03622, which is expressly incorporated by reference herein. As another option, a model (such as a stone model) may be made from the resulting impression, and the data may then be obtained by scanning the model with a scanner such as a video camera, a laser scanner, by using a mechanical profilometer that mechanically probes the model, or by use of the apparatus described in PCT Publication WO97/03622. Other options for obtaining digital data are described in U.S. Pat. No. 6,123,544, which is expressly incorporated by reference herein.

The scanner may be directly coupled to a port of a data processor. Alternatively, the scanner may be located at a remote location and may communicate the scanned data to the data processor by way of a network interface.

Figure 17:
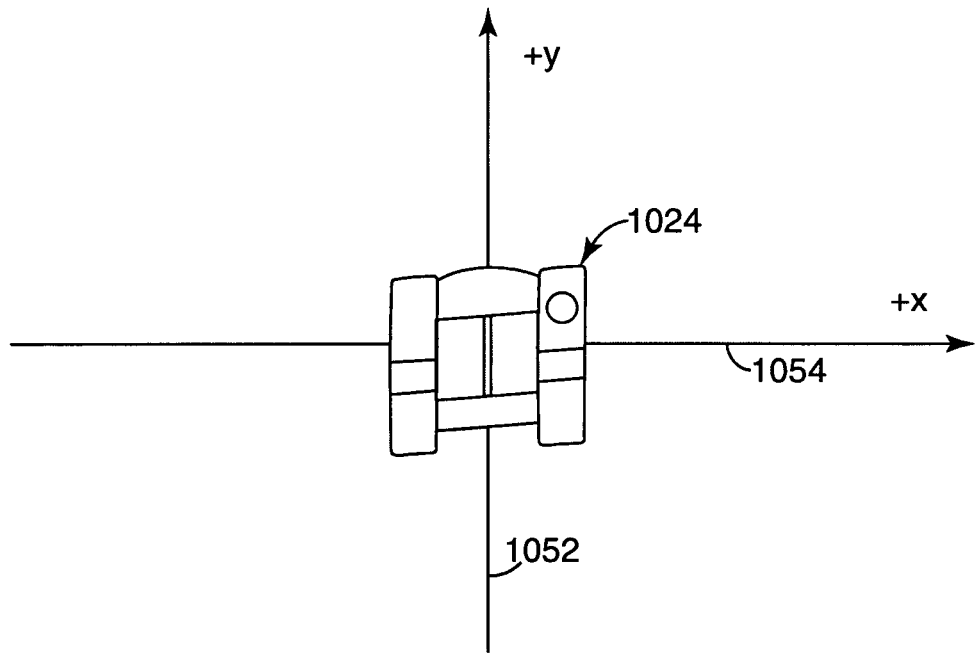
FIG. 17 is an elevational view, looking in a lingual direction, of an exemplary orthodontic appliance that may be used in the method set out in FIG. 15, additionally showing a pair of reference axes that have been placed in a certain orientation relative to the appliance.
Figure 18:
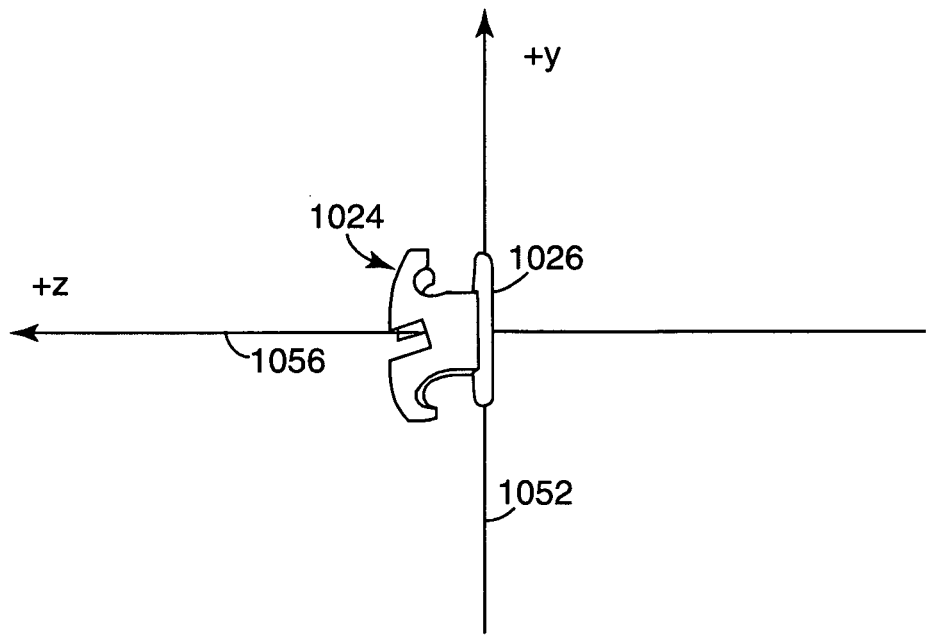
FIG. 18 is a side elevational view, looking in a mesial direction, of the appliance shown in FIG. 17 along with two reference axes.
Figure 20:
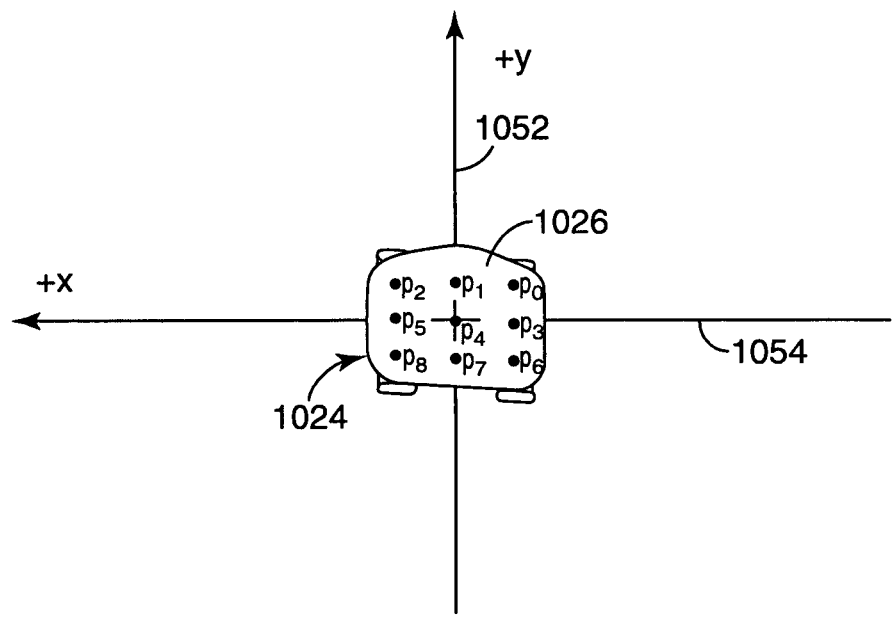
FIG. 20 is a rear elevational view, looking in a buccolabial direction, of the appliance shown in FIGS. 17 and 18, additionally showing for exemplary purposes nine points that have been designated on a base of the appliance
Figure 21:
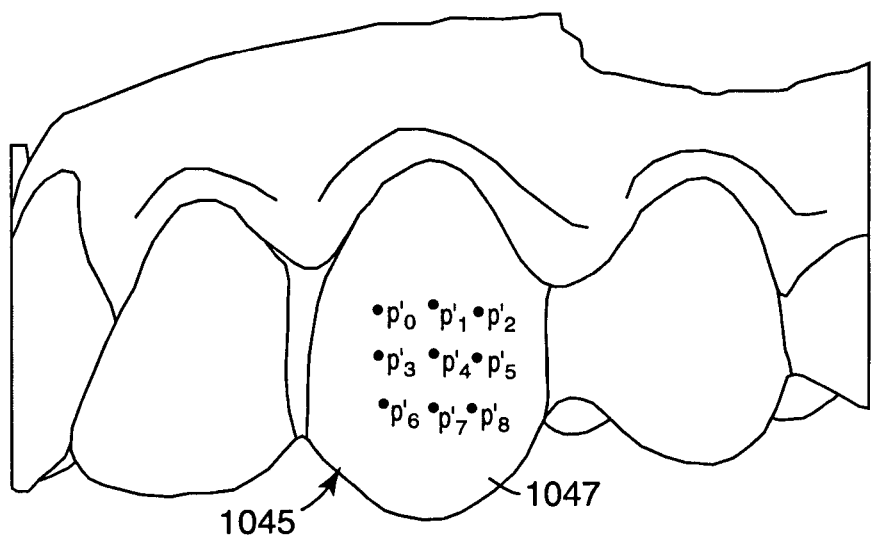
FIG. 21 is an enlarged, schematic, front elevational view of the virtual dental arch depicted in FIG. 16, additionally showing for exemplary purposes nine points that have been designated on a facial surface of the virtual cuspid tooth.

As indicated by Block 1022, three-dimensional data of a surface of an orthodontic appliance is also obtained. The appliance may be any orthodontic component that is adapted to be directly bonded to a tooth by use of an adhesive. Examples of such appliances include brackets, buccal tubes, buttons, cleats, lingual sheaths and bite planes. An example of a suitable orthodontic appliance is the bracket 1024 that is shown in FIGS. 17, 18 and 20.

The three-dimensional data of the appliance that is described in Block 1022 may be obtained by scanning the appliance with a camera or laser scanner. Preferably, however, the data is obtained from manufacturing data used to manufacture the appliance, such as a set of digital data used in automated milling machines.

Preferably, the three-dimensional data represents all exposed sections of the appliance surface, so that a visual representation of the appliance may be displayed to the practitioner as depicted in the drawings. Optionally, however, the surface may be limited to a base surface or base section of the appliance. In FIGS. 18 and 20, the base is indicated by the numeral 1026.

Conventionally, the manufacturers of orthodontic appliances attempt to make the base of directly-bonded orthodontic appliances with a shape that is similar to the expected shape of a patient's tooth, using statistical averages, in an attempt to ensure that a close, mating fit between the appliance and the tooth is obtained. Oftentimes, the shape of the base represents a compound contour that is curved along two reference axes (such as a mesial-distal reference axis and an occlusal-gingival reference axis). However, some appliances, and particularly appliances adapted for bonding to the anterior teeth, may have a shape that is flat or essentially flat.

The base of many conventional orthodontic appliances is often textured to increase the bond strength between the appliance and the adhesive. The texture may be provided by roughening the base (for example, by sandblasting the base) or by providing projections, pores, recesses, dimples or other structure integral with or otherwise connected to the body of the appliance. As another alternative, the base of the appliance may be provided with a wire mesh, similar to a screen mesh with small openings. As yet another option, the base may be provided with a number of regular or irregular particles that project outwardly for contact with the adhesive.

In instances where the appliance does not have a base surface that is relatively smooth, such as in appliances mentioned in the preceding paragraph, the set of data for the appliance base may be obtained by creating a hypothetical, smoothly curved surface. The hypothetical surface is obtained by a best fit method, such as a method that provides a curved surface touching the outer extremity of a majority of projections. Other methods of obtaining a hypothetical curved surface may also be used.

As indicated by Box 1028, a set of sample points, each defined in three-dimensional space, is obtained from the three-dimensional data representing the surface of the appliance base. The sampling of points is sufficient in number and distribution to at least roughly characterize the configuration and size (i.e., length and width) of the base. At a theoretical minimum, at least three points are needed. An example of a suitable number of points for an orthodontic appliance with a curved base is fifty. More points can be obtained in order to obtain a more accurate result, although the speed of carrying out the method may be hampered by the limitations of computer hardware.

For exemplary purposes, nine sample points designated $p_0$ to $p_8$ are shown in FIG. 20. Each of the points $p_0$ to $p_8$ lies on the surface of the base that is obtained in Block 1022. Preferably, and as shown, some of the points lie adjacent the edge of the base 1026 while at least one point lies near or on the center of the base 1026. In the example shown in FIG. 20, point $p_4$ coincides with the center of the base 1026.

Figure 19:
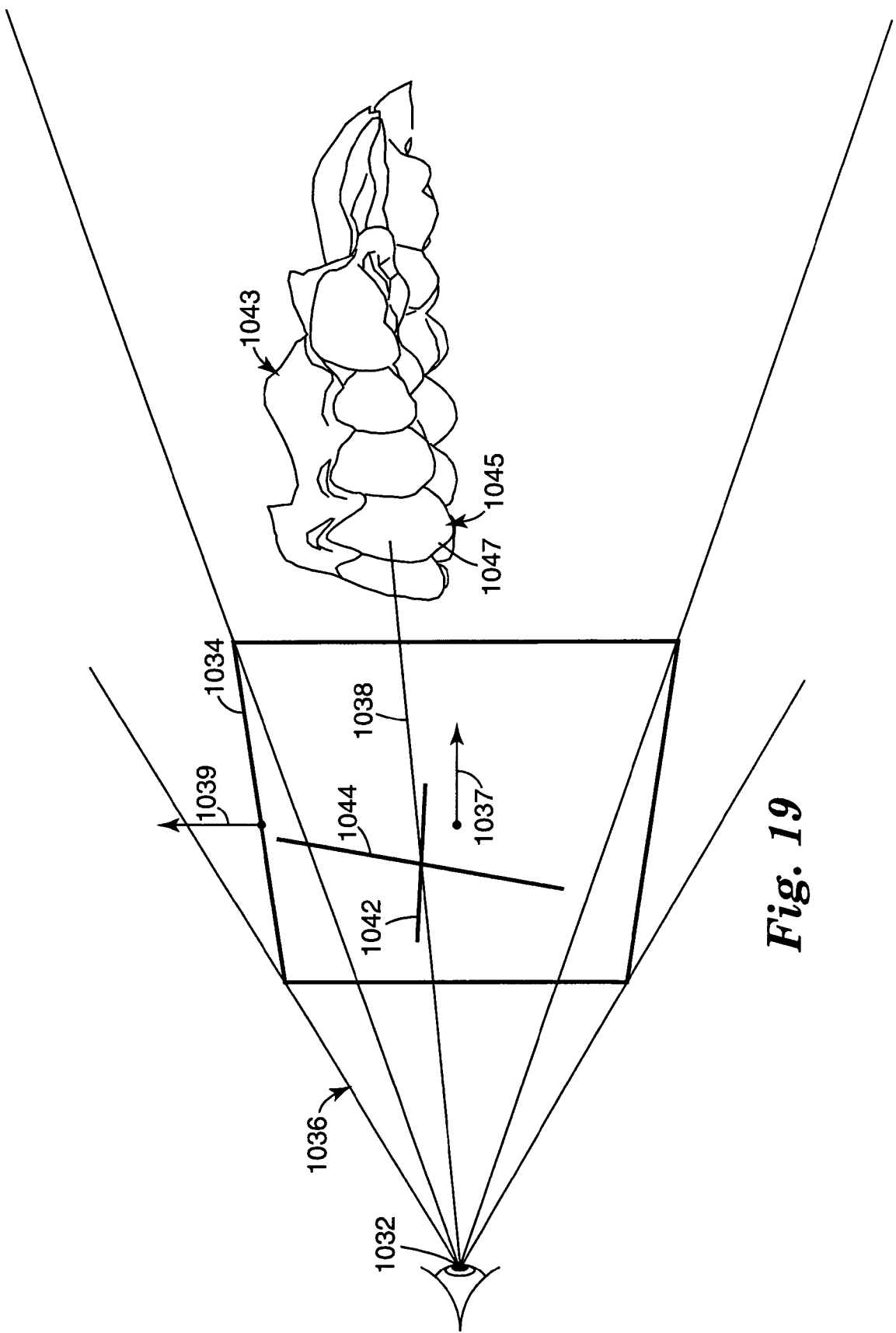
FIG. 19 is a schematic view illustrating an exemplary view-plane that is established in the method of FIG. 15.

A view frustum is then defined as indicated by Block 1030 and as schematically illustrated in FIG. 19. An eye point 1032 as shown in FIG. 19 represents the apex of the cone defined by the frustum. A two-dimensional view plane 1034 is also defined and coincides with one surface of the frustum. The view frustum is designated by the numeral 1036 in FIG. 19 and may be of any convenient shape (such as a four-sided pyramid or a right circular cone).

FIG. 19 also depicts a view plane normal vector 1041a. The vector 1041a extends in a direction perpendicular to the view plane 1034 and optionally passes through the eye point 1032. A view plane up vector 1041b is also established. The view plane up vector 1041b is parallel to the view plane 1034 and extends in an upward direction when viewed by an observer.

If, for example, the view plane 1034 is rectangular, the view plane up vector 1041b may be parallel to the left and right edges of the view plane 1034, although other orientations are also possible. The view frustum 1036 is then oriented relative to the dental arch so that the area of the arch that is intended to receive the appliance is projected onto the view plane. This is set out in Box 1039.

Next, and as described in Box 1040, a horizontal crosshair 1042 and a vertical crosshair 1044 are defined on the view plane 1034. Preferably, the intersection of the horizontal and vertical crosshairs 1042, 1044 lies within the bounds of the view plane 1034. However, the horizontal crosshair 1042 and the vertical crosshair 1044 need not actually lie horizontally and vertically, respectively, relative to the view plane up vector 1041b, nor do they need to form a right angle between them.

The line-of-sight 1038 is then defined as a ray that originates at the eye point 1032, extends to the view plane 1034 and passes through the intersection point of the crosshairs 1042, 1044. If, for example, the view frustum is a right rectangular pyramid or a right circular cone, and the crosshairs 1042, 1044 are placed at the center of the view plane, the line-of-sight 1038 will be parallel to the view plane normal vector 1043. However, other view frustums may be used, and in those instances the line-of-sight need not be parallel to the view plane normal vector 1043.

The crosshairs 1042, 1044 are then oriented in the view plane 1034 so that (1) the intersection of the crosshairs 1042, 1044 projects onto the surface of the dental arch at a location where the center of the surface of the appliance base 1026 is desired, and (2) the rotative orientation of the crosshairs 1042, 1044 matches the rotative orientation desired of the bracket 1024 about its buccolabial-lingual axis with respect to the dental arch. This act is described in Box 1048. In practice, this orientation may be achieved by use of a user controlled computer input device such as a mouse or stylus to move the crosshairs 1042 relative to the virtual arch.

Figure 16:
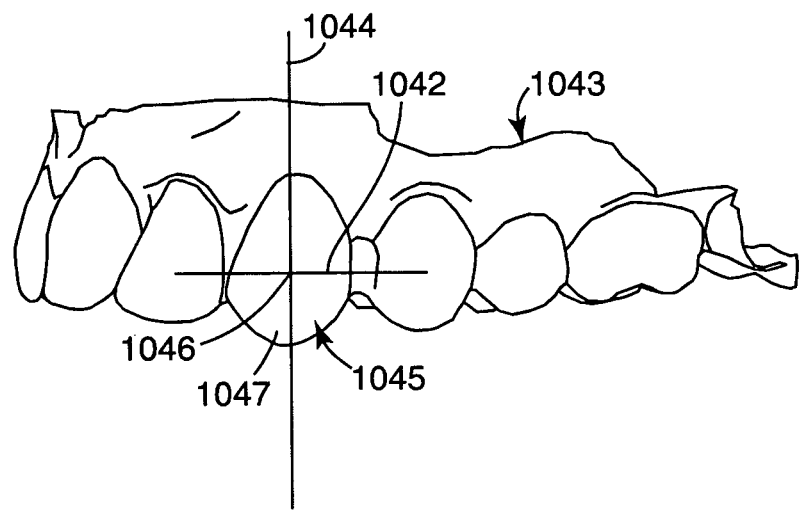
FIG. 16 is a schematic illustration looking in a lingual direction of a virtual representation of a patient's dental arch, additionally showing reference axes that have been placed in alignment with a cuspid tooth of the virtual model.

FIG. 16 illustrates a model of a patient's upper dental arch 1043 that includes an upper left cuspid tooth 1045 having a facial or buccolabial surface 1047. In FIG. 16, the crosshairs 1042, 1044 have been aligned with a location on the model of the patient's upper left cuspid tooth 1045. The particular location on the cuspid tooth 1045 may be any location according to the particular orthodontic treatment plan desired by the orthodontic practitioner.

For example, the location on the tooth that is selected for alignment with the intersection of the crosshairs 1042, 1044 may coincide with the facial axis point 1046 of the clinical crown of the cuspid tooth 1045 as shown in FIG. 16. The facial axis point is located at the intersection of the midsagittal plane of the cuspid tooth 1045 and the mid-lateral plane of the cuspid tooth 1045 at a point where the intersection of the planes meets the buccolabial tooth surface.

Figure 16A:
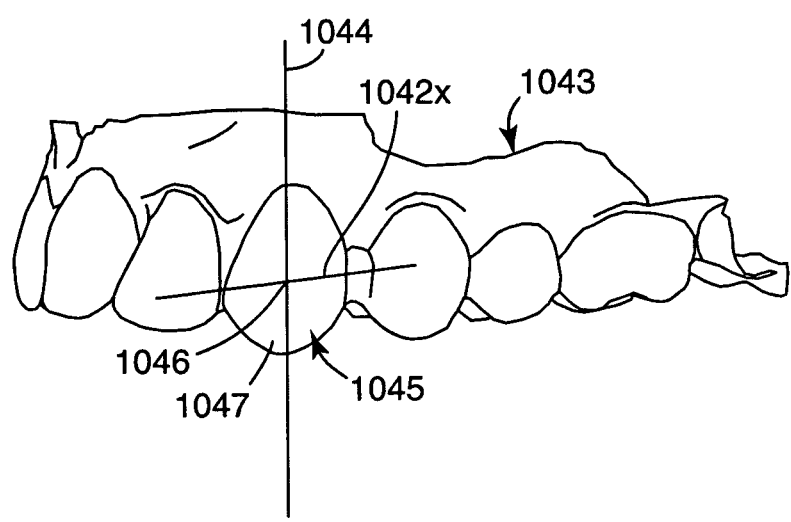
FIG. 16A is an illustration somewhat similar to FIG. 16, but showing another embodiment of the invention.

As an alternative, the crosshairs 1042, 1044 need not be perpendicular to each other. In FIG. 16A, the crosshair 1042x extends at an angle other than 90 degrees relative to the crosshair 1044. Such a practice may be desirable in instances where the selected bracket is angulated (i.e., the longitudinal axis of the archwire slot is not perpendicular to the mesial and distal sides of the bracket).

The bracket 1026 is provided with three reference axes that are depicted in FIGS. 17 and 18. These three axes include an occlusal-gingival reference axis 1052, a mesial-distal reference axis 1054 and a buccolabial-lingual reference axis 1056.

Next, the bracket 1024 is placed at a point along the line-of-sight, preferably on the labial side of the tooth if the bracket 1024 is to be placed labially, or preferably on the lingual side of the tooth if the bracket 1024 is to be placed lingually. For example, and as set out in Box 50, the bracket 1024 may be virtually placed at the apex of the view frustum 1036 such that the bracket base 1026 faces the labial surface of the cuspid tooth 1045. The bracket 1024 is also oriented so that a lingual vector of the buccolabial-lingual reference axis 1056 is collinear with the line-of-sight. In addition, the bracket 1024 is oriented such that the gingival vector of the occlusal-gingival reference axis 1052, as it is projects onto the view plane 1034, is parallel to the up vector 1041b of the view plane 1034 in instances when the arch is a maxillary arch. When the arch is a mandibular arch, the occlusal vector of the occlusal-gingival reference axis 1052 is parallel to the up vector 1041b of the view plane 1034.

The bracket 1024 is then rotated about its labio-lingual axis (i.e., the line-of-sight) as described in Box 1057. The bracket 1024 is rotated by the same angle with which the horizontal and vertical crosshairs 1042, 1044 have been rotated on the view plane 1034 to match the orientation desired of the bracket 1024 with respect to the dental arch 1043.

Figure 22:
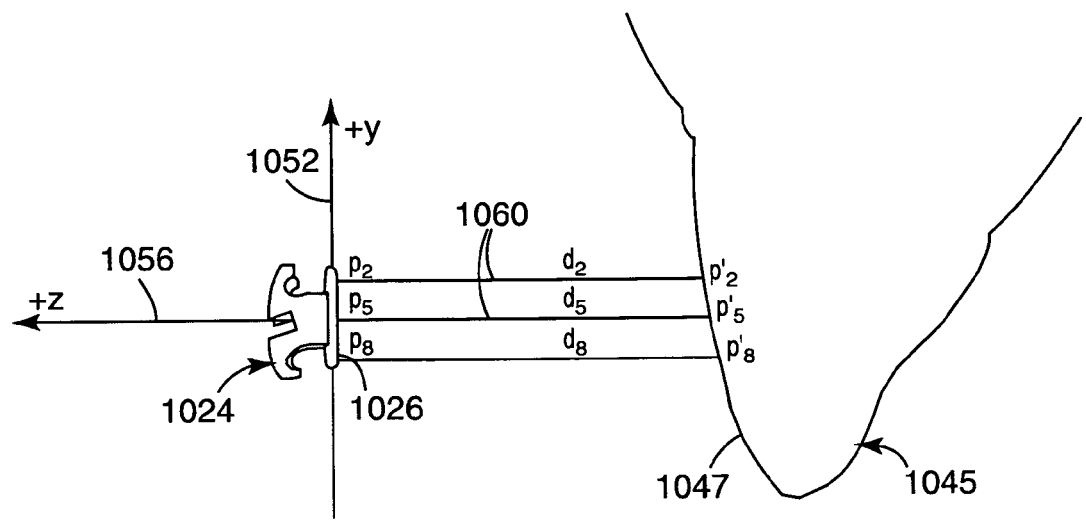
FIG. 22 is an enlarged side elevational view, looking in a mesial direction, of the appliance shown in FIGS. 16, 17 and 20 and the cuspid tooth alone that is illustrated in FIG. 21, additionally depicting three rays that extend between three of the points established on the base of the appliance and three corresponding points that have been established on the facial surface of the cuspid tooth.

Next, a first axis for rotation of the bracket 1024 is selected. In this embodiment, and as indicated by Box 1058, the mesial-distal reference axis 1054 (FIG. 17) is first selected as an axis for rotation of the bracket 1024. A set of reference lines or rays 1060 are then established as described in Box 1062. Each ray 1060 extends from one of the sample points $p_0$ to $p_8$ toward the cuspid tooth 1045. The rays 1060 are illustrated in FIG. 22.

In the illustrated embodiment, the rays 1060 extend parallel to one another and parallel to the line-of-sight toward the cuspid tooth 1045. However, other methods are possible. For example, the rays 1060 could radiate outward from a reference point such that a certain angle of divergence is present between the rays 1060. Optionally, that reference point could coincide with the center of curvature of the base 1026. As an additional option, a base 1026 having a compound curvature might have two or more of such reference points.

The method then involves the determination of points on the surface of the cuspid tooth 1045 that correspond to locations where the rays 1060 intersect the facial surface 1047 of the tooth 1045. This determination is described in Box 1064. The points on the surface of the cuspid tooth 1045 are designated $p'_0$ to $p'_8$ in FIGS. 21 and 22.

Next, and as indicated by Box 1066, the distance is determined along each of the rays 1060 between the bracket 1024 and the tooth surface 1047. Three of those distances are illustrated in FIG. 22 and are represented as $d_2$, $d_5$ and $d_8$. The distance $d_2$ represents the distance between points $p_2$ and $p'_2$, the distance $d_5$ represents the distance between point $p_5$ and $p'_5$, and so on.

Subsequently, an arithmetic function is carried out on some and preferably all of the distances determined in Block 1066. For example, and as set out in Block 1068, the mean distance of the distances determined in Block 1066 on each side of the axis of rotation of the bracket 1024 is separately calculated. For instance, if the mesial-distal axis passes through point $p_4$ of the base 1026, the mean of the distances $d_0$, $d_1$, $d_2$ and $d_5$ is calculated. Additionally, the mean of the distances $d_3$, $d_6$, $d_7$ and $d_8$ is also calculated. The difference between those two means is then determined.

Other arithmetic functions are also possible. For example, the function could be a simple summation of the distances corresponding to the rays that lie on each side of the axis of rotation (in this instance, the mesial-distal axis). As another option, the arithmetic function may be a calculation of the root mean square of the distances that lie along each side of the axis of rotation. As yet another option, the arithmetic function may be a computation of the sum of the root mean squared errors between each distance $d_0$ to $d_8$ and the mean distance when considered over the entire base 1026. In the latter option, the bracket 1024 would be rotated about the axis of rotation in a direction that reduces the sum of the mean squared errors when compared with the sum of the mean squared errors from the previous orientation. As still another option, the arithmetic function may include a calculation of the volume of at least a portion of the space between the base and the tooth, preferably using a calculation that includes one of the distance calculations mentioned above.

The bracket 1024 and the cuspid tooth 1045 are then moved relative to each other from the previous orientation (e.g., a "first" orientation) to a second orientation that is different from the first orientation as described in Box 1070. For example, the bracket 1024 may be moved to a second orientation while the cuspid tooth 1045 remains stationary. As another option, the bracket 1024 may remain stationary while the cuspid tooth 1045 moves.

Figure 23:
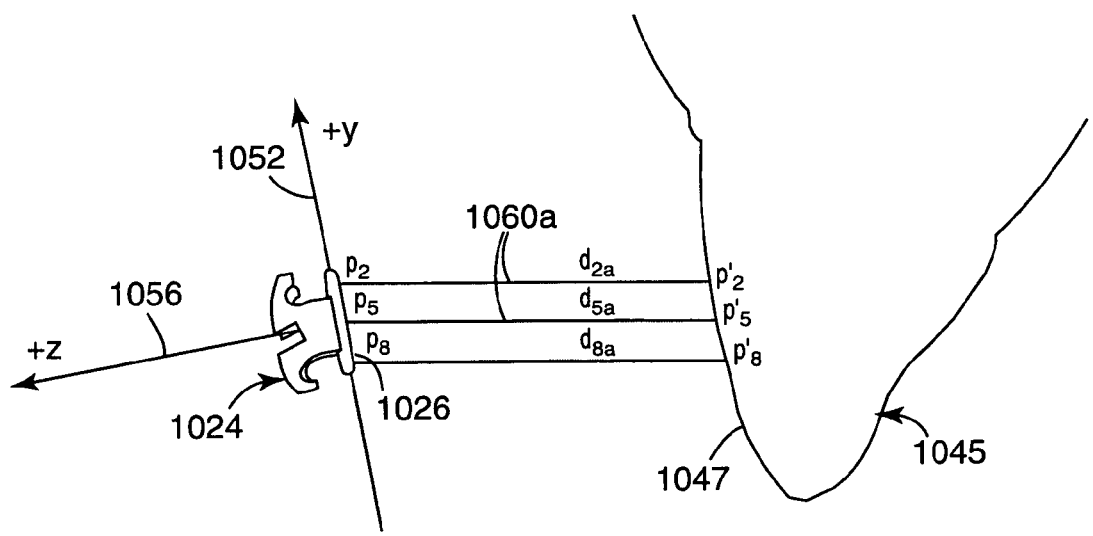
FIG. 23 is a view somewhat similar to FIG. 22 except that the relative orientation of the appliance and the tooth has been changed.

For example, and as shown by a comparison of FIGS. 22 and 23, the bracket 1024 is rotated about its mesial-distal axis 1054 from the first orientation shown in FIG. 22 to the second orientation shown in FIG. 23. The rotative movement is preferably carried out in a small, predetermined angular increment in a direction that reduces the difference between the mean distances calculated in Box 1068. Although the orientation of the bracket 1024 to the tooth 1045 has now been changed, the points $p_0$ to $p_8$ remain in the same location on the base 1026.

Next, a set of reference lines or rays 1060a are established as set out in Box 1071. Each ray 1060a extends from one of the sample points $p_0$ to $p_8$ toward the cuspid tooth 1045. In this embodiment, the rays 1060a extend parallel to each other and to the line-of-sight toward the tooth 1045 as shown in FIG. 23.

The method then involves the determination of points on the surface of the cuspid tooth 1045 that correspond to locations where the rays 1060a intersect the facial surface 1067 of the tooth 1045. This determination is described in Box 1072. In FIG. 23, three points on the facial surface 1047 are shown and are designated by the numerals $p'_{2a}$, $p'_{5a}$ and $p'_{8a}$.

The distance along the rays 1060a between each point on the base 1026 and the corresponding point on the cuspid tooth 1045 when the tooth is in the second orientation is then determined as indicated by Box 1073. This calculation is somewhat similar to the calculation set out in Box 1066. In FIG. 23, the distances $d_{2a}$, $d_{5a}$ and $d_{8a}$ are exemplified.

Subsequently, the mean of the distances between the points and along the rays 1060a on each side of the axis of rotation of the bracket 1024 is determined for the second orientation of the tooth. This calculation is set out in Box 1074 and is similar to the calculation mentioned above in connection with the first orientation of the tooth as set out in Box 1068. Box 1074 also includes the act of determining the differences of the two means.

The difference between the distances determined when the bracket 1024 and the tooth 1045 are in the first relative orientation and the distances determined when the bracket 1024 and the tooth 1045 are in the second relative orientation is then quantified. Subsequently, the bracket 1024 and the tooth 1045 are relatively moved in an arc about the reference axis in a direction such that the quantified difference is reduced. As an alternative description of the invention, the distances determined when the bracket 1024 and the tooth 1045 are in the first relative orientation and the distances determined when the bracket 1024 and the tooth 1045 are in the second relative orientation are compared in order to select the orientation corresponding overall to the smaller distances under a preselected mathematical computation, so that the direction of subsequent relative movement of the bracket 1024 and the tooth 1045 can be ascertained.

For example, and as set out in Box 1076, the difference of the means calculated in Box 1068 is then compared to the difference of the means calculated in Box 1074. If the resulting difference did not change in sign, the method returns via path 1078 to a location in the method immediately before Box 1070 and the tasks described above are repeated. If the sign did change, the method proceeds to Box 1079.

In Box 1079, the axis of bracket rotation is recalled. If the axis of rotation identified in Box 1070 was the mesial-distal reference axis 1054, the method proceeds to Box 1080, where the axis of rotation is changed to the occlusal-gingival reference axis 1052. However, if the axis of bracket rotation identified in Box 1070 was not the mesial-distal reference axis 1054, the method proceeds to Box 1082 where the axis of bracket rotation is set to the mesial-distal reference axis 1054. From either Box 1080 or Box 1082, the method proceeds to Box 1084.

As described in Box 1084, a set of rays is extended from sample points on the base 1026 of the bracket 1024 in a direction toward the cuspid tooth 1045. Optionally, the rays are parallel to each other and parallel to the line-of-sight. Preferably, each ray extends from the sample points previously identified on the bracket base 1026 such as points $p_0$ to $p_8$. Each ray intersects the surface 1047 of the cuspid tooth 1045 at a point.

Box 1086 represents the determination of the location of the points on the surface of the cuspid tooth 1045. The length of each line segment between the points is then determined as described in Box 1088. In particular, the distance between each sample point on the base 1026 and the corresponding point on the surface of the cuspid tooth 1045 is calculated.

Subsequently, the mean of the distances determined in Box 1088 on each side of the axis of bracket rotation is calculated and the difference between the two means is computed. This calculation is indicated by Box 1090 and is similar to the calculation set out in Box 1068. However, the axis of bracket rotation in this instance may be the occlusal-gingival axis 1052 (if proceeding from Box 1080) or may be the mesial-distal reference axis 1054 (if proceeding from Box 1082).

The method then proceeds to Box 1092. If the difference in mean distances that are calculated in Box 1090 is greater than a predetermined tolerance, the method returns via paths 1094 and 1078 to the location immediately preceding Box 1070. However, if the difference between the mean distances calculated in Box 1090 is less than a predetermined tolerance, additional rotations are not needed and the method proceeds via path 1096 to Box 1098.

The bracket 1024 is then translated along the line-of-sight toward the cuspid tooth 1045 as described in Box 1098. The bracket advances toward the cuspid tooth 1045 a distance that is equal to the minimum distance determined in Box 1088. Optionally, translation of the bracket toward the cuspid tooth 1034 may be reduced by the expected thickness of adhesive used to bond the bracket 1024 to the tooth surface.

Figure 24:
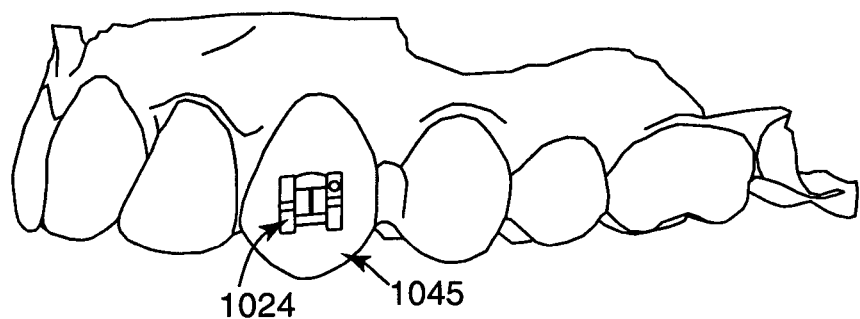
FIG. 24 is a schematic elevational view of the dental arch shown in FIG. 16 along with the appliance shown in FIGS. 17, 18 and 20, wherein the appliance has been placed on the tooth at a desired location and in a desired orientation.

FIG. 24 is an illustration of the bracket 1024 that has been placed at the desired location on the cuspid tooth 1045. In this view, the bracket 1024 is illustrated in its optimal orientation relative to the cuspid tooth 1045 so that a close, mating fit between the base 1026 and the tooth surface 1047 is attained. The computer carrying out the method then virtually "detaches" the bracket 1024 from the line-of-sight 1038 so that other appliances may be placed on respective teeth as desired.

Figure 25:
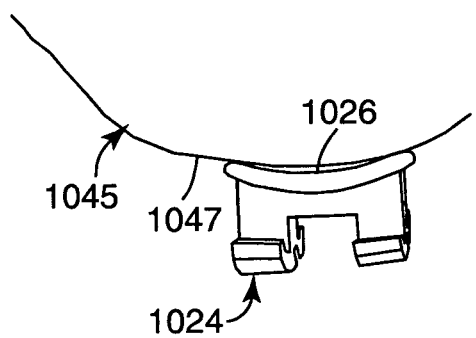
FIG. 25 is a fragmentary, enlarged top view, looking in an occlusal direction, of the appliance and cuspid tooth shown in FIG. 24, illustrating the fit of the base of the appliance against the facial surface of the tooth.

FIG. 25 is an enlarged, fragmentary top view of the bracket 1024 and the adjacent labial surface of the cuspid tooth 1045. In this illustration, it can be observed that a small gap is present between the base 1026 and the surface 1047 of the cuspid tooth 1045 in a location near the middle of the base 1026. The gap is present because of the difference in curvature between the tooth surface 1047 and the base 1026, even though the orientation of the bracket 1024 relative to the cuspid tooth 1045 has been selected by the method set out above in order to achieve a close fit between the bracket 1024 and the tooth 1045.

Figure 26:
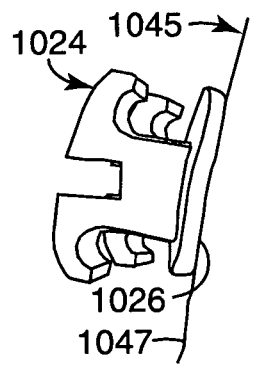
FIG. 26 is a view somewhat similar to FIG. 25 except that FIG. 26 is a side elevational view of the appliance, looking in a mesial direction.

FIG. 26 is an enlarged, side elevational view showing the bracket 1024 and a portion of the cuspid tooth 1045, looking in a mesial direction. In this view, the curvature of the base 1026 closely matches the curvature of the adjacent section of the tooth 1045 and no gap along the mesial edge of the base 1026 is apparent.

Figure 27:
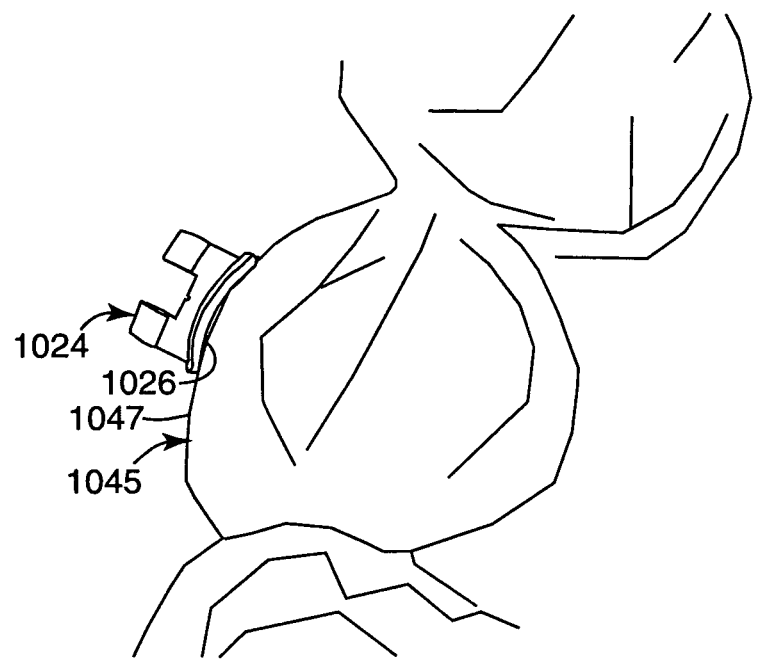
FIG. 27 is a view somewhat similar to FIGS. 25 and 26, except that FIG. 27 is a bottom view of the appliance, looking in a gingival direction.

FIG. 27 is an enlarged bottom view of the bracket 1024 and the cuspid tooth 1045, looking at the tooth in a gingival direction. The curvature of the base 1026 is somewhat different than the curvature of adjacent portions of the tooth 1045 in this view, and as a consequence, a slight gap is observed. However, the use of the method described above tends to optimize the relative orientation between the bracket 1024 and the tooth 1045 such that a relatively close fit is attained.

Optionally, the computer program carrying out the method described above may also enable the user to shift the appliance on the tooth to a preferred orientation, using translational movement along the surface of the tooth as well as rotative movement about its labio-lingual axis or the Z axis as shown, e.g., in FIG. 18. The user may shift the appliance manually (for example, by a click and drag motion of a computer mouse) or automatically (for example, by specifying that the archwire slot of the appliance should extend in a direction parallel to the occlusal plane and be located a certain distance from the occlusal edge of the tooth). Such adjustments are preferably carried out simultaneously with the steps set out above in FIG. 15, so that the appliance remains in an optimal fit with respect to the tooth surface as the adjustments are made.

Figure 28:
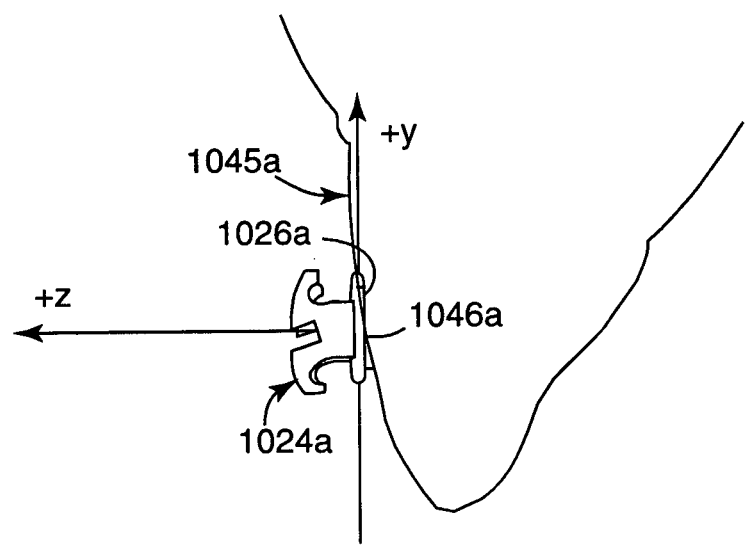
FIG. 28 is a view somewhat similar to FIG. 22 but showing a somewhat different representation of the relative orientations of the appliance and the tooth in accordance with another embodiment of the invention.

FIG. 28 is an illustration of an alternate embodiment of the invention, wherein the method is carried out as described above except the appliance is initially located next to the tooth surface. In particular, the center of a base 1026a of a bracket 1024a is placed in a location tangent to the facial axis point 1046a in this embodiment. Consequently, as the bracket is rotated about its mesial-distal axis as exemplified above by Box 1070, some of the sample points on the bracket base may exist on a lingual side of the facial surface of cuspid tooth 1045a. As shown, other sample points may exist in a direction labially of the facial surface of cuspid tooth 1045a.

The method described earlier in connection with FIGS. 16-27 is used in conjunction with the embodiment exemplified by FIG. 28 except that absolute values of the distances are calculated. In addition, in the final orientation of the bracket 1024 relative to the tooth 1045, the bracket 1024 is translated in a buccolabial direction so that none of the sample points lie on a lingual side of the facial surface of the cuspid tooth 1045.

A number of variations to the methods described above are also possible and will be apparent to those skilled in the art. For example, the method may be used in conjunction with appliances that are to be bonded to the lingual surfaces of the patient's teeth. Also, reference axes and points of reference (such as the facial axis point) may be different from those set out above.

Moreover, the method described above may be changed by varying the amount of rotative movement in accordance with the attained result. For example, the increment of rotative movement initially may be relatively large and then reduced in subsequent steps. For example, the amount of rotative movement can be reduced once a difference in sign is noted as determined in Box 1076.

Various embodiments of the invention have been described. These and other embodiments are within the scope of the following claims.

The invention claimed is:

1. A method comprising:
    rendering a digital representation of at least a portion of a tooth within a three-dimensional (3D) virtual environment;
    receiving a desired occlusal height for an orthodontic appliance associated with the tooth;
    automatically adjusting the orthodontic appliance from a current occlusal height to the desired occlusal height on the tooth within the 3D virtual environment along a translation axis defined relative to the orthodontic appliance; and
    displaying a digital representation of the orthodontic appliance at the desired occlusal height.

2. The method of claim 1, further comprising displaying the orthodontic appliance and the tooth within the 3D virtual environment as a visual aid to a practitioner in the placement of the orthodontic appliance on the tooth.

3. The method of claim 1, wherein automatically adjusting the orthodontic appliance comprises determining the current occlusal height of the orthodontic appliance.

4. The method of claim 3, wherein automatically adjusting the orthodontic appliance comprises comparing the current occlusal height to the desired occlusal height.

5. The method of claim 4, wherein automatically adjusting the orthodontic appliance comprises adjusting the current occlusal height based on the comparison.

6. The method of claim 1, wherein automatically adjusting the orthodontic appliance comprises:
    determining a difference between a current occlusal height of the orthodontic appliance and the desired occlusal height;
    comparing the difference to an allowable error; and
    adjusting the current occlusal height to the desired occlusal height when the difference is greater than the allowable error.

7. The method of claim 1, wherein automatically adjusting the orthodontic appliance comprises:
    determining a translation distance; and
    translating the orthodontic appliance by the translation distance along the translation axis.

8. The method of claim 7, wherein determining the translation distance comprises defining the translation distance as $(h_i - h^*)/\cosine(\alpha)$, wherein $h_i$ is the current occlusal height, $h^*$ is the desired occlusal height, and $\alpha$ is a bracket angulation.

9. The method of claim 8, further comprising defining the translation axis as an intersection of an appliance slot plane and an appliance base plane.

10. The method of claim 1, further comprising:
    determining an occlusal-most point of the tooth; and
    determining the desired occlusal height relative to the occlusal-most point of the tooth.

11. The method of claim 1, further comprising:
    determining an occlusal-most point of a dental arch in which the tooth is one of a plurality of teeth; and
    determining the desired occlusal height relative to the occlusal-most point of the dental arch.

12. The method of claim 1, further comprising:
determining at least two occlusal-most points of the tooth;
calculating an average of the at least two occlusal-most points of the tooth; and
determining the desired occlusal height relative to the average of the occlusal-most points of the tooth.

13. The method of claim 1, further comprising:
rendering a digital representation of a dental arch in which the tooth is one of a plurality of teeth within the 3D virtual environment;
determining an occlusal-most plane of the dental arch; and
determining the desired occlusal height relative to the occlusal-most plane of the dental arch.

14. The method of claim 1, further comprising automatically refitting the orthodontic appliance to attain a fit between a base of the orthodontic appliance and a surface of the tooth.

15. The method of claim 1, further comprising:
rendering a digital representation of a dental arch in which the tooth is one of a plurality of teeth within the 3D virtual environment; and
receiving desired occlusal height data from a practitioner for each of the teeth in the dental arch.

16. The method of claim 15, wherein each of the teeth in the dental arch has an associated orthodontic appliance, and further comprising automatically adjusting the occlusal height of each orthodontic appliance on the associated tooth within the 3D virtual environment based on the desired occlusal height data.

17. The method of claim 1, wherein the desired occlusal height is received from a practitioner via a user interface.

18. The method of claim 1, wherein the desired occlusal height is selected from a standardized set of occlusal heights.

19. The method of claim 1, wherein the desired occlusal height is part of a customized set of occlusal heights.

20. The method of claim 1, wherein the orthodontic appliance comprises an orthodontic bracket, a buccal tube, a sheath, a button or an arch wire.

21. The method of claim 1, wherein the tooth comprises an anterior tooth or a posterior tooth.

22. The method of claim 1, wherein the tooth comprises a multi-cusp tooth.

23. The method of claim 1, wherein automatically adjusting the orthodontic appliance comprises translating the orthodontic appliance along the translation axis by a translation distance based on the current occlusal height, the desired occlusal height and a bracket angulation.

24. The method of claim 1, wherein automatically adjusting the orthodontic appliance comprises automatically adjusting an orthodontic appliance from a current occlusal height to a desired occlusal height on the tooth within the 3D virtual environment along a translation axis defined relative to a bracket base coordinate system.

25. The method of claim 24, further including defining the bracket base coordinate system as having an origin at a center of a base of the orthodontic appliance and having a y-axis parallel to a mid-sagittal plane of the tooth.

26. The method of claim 1, wherein automatically adjusting the orthodontic appliance further comprises:
determining a difference between the current occlusal height of the orthodontic appliance and the desired occlusal height of the orthodontic appliance as measured relative to a bracket slot coordinate system;
determining a bracket translation distance based on the difference and a bracket angulation; and
translating the orthodontic appliance by the bracket translation distance relative to the translation axis.

27. The method of claim 26, wherein translating the orthodontic appliance comprises translating the orthodontic appliance by the bracket translation distance relative to the translation axis defined as an intersection of a bracket slot plane and a bracket base plane.

28. The method of claim 26, further including defining the bracket slot coordinate system as having an origin at a center of a slot of the orthodontic appliance and having an x-axis parallel to the slot.

29. The method of claim 28, further including defining the bracket angulation as an angle between a y-axis of the bracket slot coordinate system and a y-axis of a bracket base coordinate system.

30. The method of claim 29, further including defining the bracket base coordinate system as having an origin at a center of a base of the orthodontic appliance and having a y-axis parallel to a mid-sagittal plane of the tooth.

31. A system comprising:
a computing device; and
modeling software executing on the computing device, wherein the modeling software comprises:
a rendering engine that renders a digital representation of at least a portion of a tooth within a three-dimensional (3D) virtual environment;
an occlusal height control module that automatically adjusts an orthodontic appliance from a current occlusal height to a desired occlusal height on the tooth within the 3D virtual environment along a translation axis defined relative to the orthodontic appliance; and
a user interface that displays a digital representation of the orthodontic appliance at the desired occlusal height.

32. The system of claim 31, further comprising a user interface to display the orthodontic appliance and the tooth within the 3D virtual environment.

33. The system of claim 31, wherein the occlusal height control module:
determines the current occlusal height of the orthodontic appliance;
compares the current occlusal height to the desired occlusal height; and
adjusts the current occlusal height based on the comparison.

34. The system of claim 33, wherein the occlusal height control module:
determines a difference between the current occlusal height and the desired occlusal height;
compares the difference to an allowable error; and
adjusts the current occlusal height to the desired occlusal height when the difference is greater than the allowable error.

35. The system of claim 34, wherein the occlusal height control module:
determines a translation distance; and
translates the orthodontic appliance by the translation distance along the translation axis.

36. The system of claim 35, wherein the translation distance is defined as $(h_i - h^*)/\cosine(\alpha)$, wherein $h_i$ is the current occlusal height, $h^*$ is the desired occlusal height, and $\alpha$ is a bracket angulation.

37. The system of claim 31, wherein the translation axis is defined as an intersection of an appliance slot plane and an appliance base plane.

38. The system of claim 31, wherein the occlusal height control module determines an occlusal-most point of the tooth and determines the desired occlusal height relative to the occlusal-most point of the tooth.

39. The system of claim 31, wherein the occlusal height control module further:
    determines an occlusal-most point of a dental arch in which the tooth is one of a plurality of teeth; and
    determines the desired occlusal height relative to the occlusal-most point of the dental arch.

40. The system of claim 31, wherein the occlusal height control module further:
    determines at least two occlusal-most points of the tooth;
    calculates an average of the at least two occlusal-most points of the tooth; and
    determines the desired occlusal height relative to the average of the occlusal-most points of the tooth.

41. The system of claim 31, wherein the occlusal height control module determines an occlusal-most plane of a dental arch in which the tooth is one of a plurality of teeth and determines the desired occlusal height relative to the occlusal-most plane of the dental arch.

42. The system of claim 41, further comprising:
    a database to store data that describes attributes for types of orthodontic appliances that may be selected by the practitioner,
    wherein the occlusal height control module controls the occlusal height of the orthodontic appliance based on the stored attributes.

43. The system of claim 42, wherein the database is located remote from the computing device and coupled to the computing device via a network.

44. The system of claim 42, wherein the attributes comprise one or more of dimensions, slot locations, torque angles, and angulations for the types of orthodontic appliances.

45. The system of claim 31, wherein the occlusal height control module refits the orthodontic appliance to attain a fit between a base of the orthodontic appliance and a surface of the tooth after adjusting the orthodontic appliance to attain the desired occlusal height.

46. The system of claim 31, wherein the orthodontic appliance comprises an orthodontic bracket, a buccal tube, a sheath, a button or an arch wire.

47. The system of claim 31, wherein the tooth comprises an anterior tooth or a posterior tooth.

48. The system of claim 31, wherein the tooth comprises a multi-cusp tooth.

49. The system of claim 31, further comprising:
    a user interface that receives input from the practitioner regarding the desired occlusal height;
    wherein the occlusal height control module adjusts the occlusal height of the orthodontic appliance within the 3D virtual environment in accordance with the desired occlusal height.

50. The system of claim 31, further comprising a database that stores desired occlusal height data for each tooth in a dental arch.

51. The system of claim 31, further comprising a database that stores a set of standardized occlusal heights from which the desired occlusal height is selected.

52. The system of claim 31, wherein the occlusal height control module translates the orthodontic appliance along the translation axis by a translation distance based on the current occlusal height, the desired occlusal height and a bracket angulation.

53. The system of claim 31, wherein the occlusal height control module defines the translation axis relative to a bracket base coordinate system.

54. The system of claim 53, wherein the occlusal height control module further defines the bracket base coordinate system as having an origin at a center of a base of the orthodontic appliance, and having a y-axis parallel to a mid-sagittal plane of the tooth.

* * * * *